United States Patent
Urakawa et al.

(10) Patent No.: US 10,264,166 B2
(45) Date of Patent: Apr. 16, 2019

(54) INTRACORPOREAL-MONITORING CAMERA SYSTEM, SUPPORT TUBE FOR INTRACORPOREAL-MONITORING CAMERA SYSTEM, AND CABLE HOLDER FOR INTRACORPOREAL-MONITORING CAMERA SYSTEM

(71) Applicant: Sharp Kabushiki Kaisha, Osaka-shi, Osaka (JP)

(72) Inventors: Kei Urakawa, Osaka (JP); Toshihisa Gotoh, Osaka (JP); Tsuguhisa Inoue, Osaka (JP); Kishoh Takamatsu, Osaka (JP); Hitoshi Aoki, Osaka (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 249 days.

(21) Appl. No.: 14/917,064

(22) PCT Filed: Oct. 31, 2014

(86) PCT No.: PCT/JP2014/079085
§ 371 (c)(1),
(2) Date: Mar. 7, 2016

(87) PCT Pub. No.: WO2015/064743
PCT Pub. Date: May 7, 2015

(65) Prior Publication Data
US 2016/0234408 A1    Aug. 11, 2016

(30) Foreign Application Priority Data

Oct. 31, 2013  (JP) ................................ 2013-227571

(51) Int. Cl.
*A61B 1/00* (2006.01)
*H04N 5/225* (2006.01)
(Continued)

(52) U.S. Cl.
CPC ....... *H04N 5/2253* (2013.01); *A61B 1/00018* (2013.01); *A61B 1/00073* (2013.01);
(Continued)

(58) Field of Classification Search
CPC ............ A61B 1/00018; A61B 1/00066; A61B 1/00073; A61B 1/00101; A61B 1/00105;
(Continued)

(56) References Cited

U.S. PATENT DOCUMENTS 4,323,304 A * 4/1982 Ishii .................... A61B 1/00128
396/17
5,643,175 A * 7/1997 Adair ................. A61B 1/00073
600/123

(Continued)

FOREIGN PATENT DOCUMENTS

JP    52-168297 U    12/1977
JP    2007-125180 A    5/2007
(Continued)

OTHER PUBLICATIONS

Aoki et al., "Camera System for Monitoring Inside of Body", U.S. Appl. No. 15/546,291, filed Jul. 26, 2017.
(Continued)

*Primary Examiner* — Timothy J Neal
(74) *Attorney, Agent, or Firm* — Keating & Bennett, LLP

(57) ABSTRACT

An intracorporeal-monitoring camera system provided with a support tube whose one end is introduced in a body, an imaging portion that is joined to the support tube in the body, a joining portion that joins the imaging portion and the support tube together, a cable that is connected with the imaging portion and drawn out to an outside of the body through the support tube, and a control system that is provided on the outside of the body, connected with the cable, and includes at least a display device. A slit is formed (Continued)

in the support tube so that the cable is placed in the support tube from a side of the support tube.

16 Claims, 15 Drawing Sheets

(51) Int. Cl.
| | |
|---|---|
| *G02B 23/24* | (2006.01) |
| *A61B 1/05* | (2006.01) |
| *A61B 1/045* | (2006.01) |
| *A61B 1/313* | (2006.01) |
| *H04N 7/10* | (2006.01) |
| *A61B 1/12* | (2006.01) |
| *H04N 5/232* | (2006.01) |

(52) U.S. Cl.
CPC ...... *A61B 1/00105* (2013.01); *A61B 1/00114* (2013.01); *A61B 1/045* (2013.01); *A61B 1/05* (2013.01); *A61B 1/051* (2013.01); *A61B 1/128* (2013.01); *A61B 1/3132* (2013.01); *G02B 23/2476* (2013.01); *H04N 5/2252* (2013.01); *H04N 5/2256* (2013.01); *H04N 7/10* (2013.01); *A61B 1/00066* (2013.01); *A61B 1/00101* (2013.01); *H04N 5/23203* (2013.01); *H04N 5/23293* (2013.01); *H04N 2005/2255* (2013.01)

(58) Field of Classification Search
CPC ....... A61B 1/00114; A61B 1/045; A61B 1/05; A61B 1/051; A61B 1/128; A61B 1/3132; G02B 23/2476; H04N 2005/2255; H04N 5/2252; H04N 5/2253; H04N 5/2256; H04N 5/23203; H04N 5/23293; H04N 7/10; H04N 5/25203
See application file for complete search history.

(56) References Cited

U.S. PATENT DOCUMENTS

| | | | | |
|---|---|---|---|---|
| 9,427,255 | B2* | 8/2016 | Griffith | A61B 1/00158 |
| 2004/0133076 | A1* | 7/2004 | Kobayashi | A61B 1/00016 |
| | | | | 600/175 |
| 2007/0100201 | A1 | 5/2007 | Komiya et al. | |
| 2007/0255100 | A1* | 11/2007 | Barlow | A61B 1/0005 |
| | | | | 600/114 |
| 2008/0255458 | A1* | 10/2008 | Dunki-Jacobs | A61B 5/0071 |
| | | | | 600/476 |
| 2008/0309758 | A1 | 12/2008 | Karasawa et al. | |
| 2008/0312499 | A1* | 12/2008 | Handa | A61B 1/0005 |
| | | | | 600/109 |
| 2009/0306470 | A1* | 12/2009 | Karasawa | A61B 1/04 |
| | | | | 600/103 |
| 2010/0036199 | A1* | 2/2010 | Karasawa | A61B 1/00085 |
| | | | | 600/109 |
| 2010/0076259 | A1* | 3/2010 | Asada | A61B 1/00096 |
| | | | | 600/102 |
| 2010/0113872 | A1 | 5/2010 | Asada et al. | |
| 2011/0046440 | A1 | 2/2011 | Asada et al. | |
| 2011/0046445 | A1* | 2/2011 | Asada | A61B 1/041 |
| | | | | 600/158 |
| 2012/0016197 | A1* | 1/2012 | Turnbull | A61B 1/00105 |
| | | | | 600/109 |
| 2012/0050511 | A1* | 3/2012 | Takahashi | A61B 1/00114 |
| | | | | 348/65 |
| 2012/0123463 | A1* | 5/2012 | Jacobs | A61B 17/00234 |
| | | | | 606/191 |
| 2014/0088360 | A1* | 3/2014 | Kawaura | A61B 1/0052 |
| | | | | 600/110 |
| 2014/0114124 | A1* | 4/2014 | Dresher | A61B 1/05 |
| | | | | 600/103 |
| 2014/0135576 | A1* | 5/2014 | Hebert | A61B 1/0057 |
| | | | | 600/109 |
| 2014/0243597 | A1* | 8/2014 | Weisenburgh, II | A61B 1/00158 |
| | | | | 600/112 |
| 2014/0284751 | A1* | 9/2014 | Kamei | H01L 27/14618 |
| | | | | 257/443 |

FOREIGN PATENT DOCUMENTS

| | | |
|---|---|---|
| JP | 2009-72368 A | 4/2009 |
| JP | 4472727 B2 | 6/2010 |
| JP | 4599474 B1 | 12/2010 |
| JP | 2012-239519 A | 12/2012 |
| WO | 2015/020124 A1 | 2/2015 |

OTHER PUBLICATIONS

Gotoh el al., "In-Body Monitoring Camera System and Support Tube for In-Body Monitoring-Camera System", U.S. Appl. No. 14/899,269, filed Dec. 17, 2015.

Inoue et al., "In-Vivo Monitoring Camera System, and Support Tube for In-Vivo Monitoring Camera System", U.S. Appl. No. 15/031,777, filed Apr. 25, 2016.

Urakawa et al., "Camera System for Monitoring Inside of Body, Accessory for Support Tube of Camera System for Monitoring Inside of Body, Fixing Tool for Camera System for Monitoring Inside of Body, and Method for Installing Camera System for Monitoring Inside of Body", U.S. Appl. No. 15/031,816, filed Apr. 25, 2016.

Aoki et al., "Camera System for Monitoring Inside of Body and Auxiliary Device and Method for Installing Imaging Apparatus for Monitoring Inside of Body", U.S. Appl. No. 15/111,514, filed Jul. 14, 2016.

Aoki et al., "In-Body Monitoring Camera System and Camera Unit", U.S. Appl. No. 15/129,044, filed Sep. 26, 2016.

Aoki et al., "Camera System for Monitoring Inside of Body and Auxiliary Tool Set", U.S. Appl. No. 15/112,726, filed Jul. 20, 2016.

Official Communication issued in corresponding International Application PCT/JP2014/079085, dated May 29, 2015.

* cited by examiner

INTRACORPOREAL-MONITORING CAMERA SYSTEM, SUPPORT TUBE FOR INTRACORPOREAL-MONITORING CAMERA SYSTEM, AND CABLE HOLDER FOR INTRACORPOREAL-MONITORING CAMERA SYSTEM

TECHNICAL FIELD

The present invention relates to an intracorporeal-monitoring camera system that includes an imaging portion which may be introduced in a body, a support tube for the intracorporeal-monitoring camera system, and a cable holder for the intracorporeal-monitoring camera system.

BACKGROUND ART

Endoscopic surgery is a minimally invasive surgery that performs examinations and curative treatments without a laparotomy on a patient. In the endoscopic surgery, treatment instruments such as forceps and an endoscope are separately introduced in a body cavity of the patient, and an operator has an image at a tip portion of the treatment instrument inserted in the body cavity in an observation visual field of the endoscope and performs treatment work while observing, by the endoscope, a treatment state of an affected site by the treatment instrument. In the endoscopic surgery, the treatment instruments and the endoscope are introduced in the body cavity through a pipe punctured through a body wall (for example, an abdominal wall) in an abdomen or the like of the patient. The pipe is a tubular member, which is commonly referred to as a trocar.

The operator enlarges an image by making the endoscope approach an organ and thereby performs incision or suture of the organ. However, the visual field of the operator becomes very narrow. Thus, a device is demanded by which a state of the outside of the working area (for example, motion of the treatment instrument on the outside of the working area, a state of bleeding, and a residual state of residues such as gauze) may be widely perceived.

In consideration of such a demand, PTL 1 discloses a device that directly inserts a connector electrode having a needle shape in the abdominal wall and joins the connector electrode to a camera in the body.

Further, PTL 2 discloses a device which inserts a camera unit and a communication cable to be joined thereto through a trocar, draws out a needle and the communication cable to the outside of the body through a hole in the abdominal wall in a state where an end of the communication cable is caught by the needle inserted through the hole in the abdominal wall, and thereby fixes the communication cable.

CITATION LIST

Patent Literature

PTL 1: Japanese Patent No. 4472727 (issued on Jun. 2, 2010)
PTL 2: Japanese Patent No. 4599474 (issued on Dec. 15, 2010)

SUMMARY OF INVENTION

Technical Problem

In PTL 1, because the connector electrode in the needle shape is directly inserted in the abdominal wall and the connector electrode is joined to the camera in the body, a foreign object may enter a joining portion between the connector electrode and the camera, resulting in electrical connection failure.

In PTL 2, the communication cable is drawn out to the outside of the body and fixed. However, it is difficult to gain the joint strength between the communication cable and the camera unit due to the properties of the communication cable and also difficult to change the direction of the camera unit from the outside of the body.

The present invention suggests an intracorporeal-monitoring camera system that is highly reliable and easy to use.

Solution to Problem

An intracorporeal-monitoring camera system includes: a support tube whose one end is introduced in a body; an imaging portion that is joined to the support tube in the body; a joining portion that joins the imaging portion and the support tube together; a cable that is connected with the imaging portion and drawn out to an outside of the body through the support tube; and a control system that is provided on the outside of the body, connected with the cable, and includes at least a display device, in which a slit is formed in the support tube so that the cable is placed in the support tube from a side of the support tube.

Advantageous Effects of Invention

In one embodiment of the intracorporeal-monitoring camera system, the cable may easily be placed through an internal portion of the support tube via the slit, and the imaging portion may be joined to the support tube in the body in a state where the cable is placed through the support tube. Accordingly, the supporting force for the imaging portion is enhanced, connection failure between the imaging portion and the cable is less likely to occur, and the reliability is high. Further, an operator may change the direction of the imaging portion in the body via the support tube and may thus easily use the intracorporeal-monitoring camera system. In addition, the support tube may be fixed, and the operator does not have to support the support tube.

BRIEF DESCRIPTION OF DRAWINGS

FIG. 6(*c*) is a top cross-sectional view that illustrates the relationship between a cable connector and the support tube.

DESCRIPTION OF EMBODIMENTS

Figure 1:
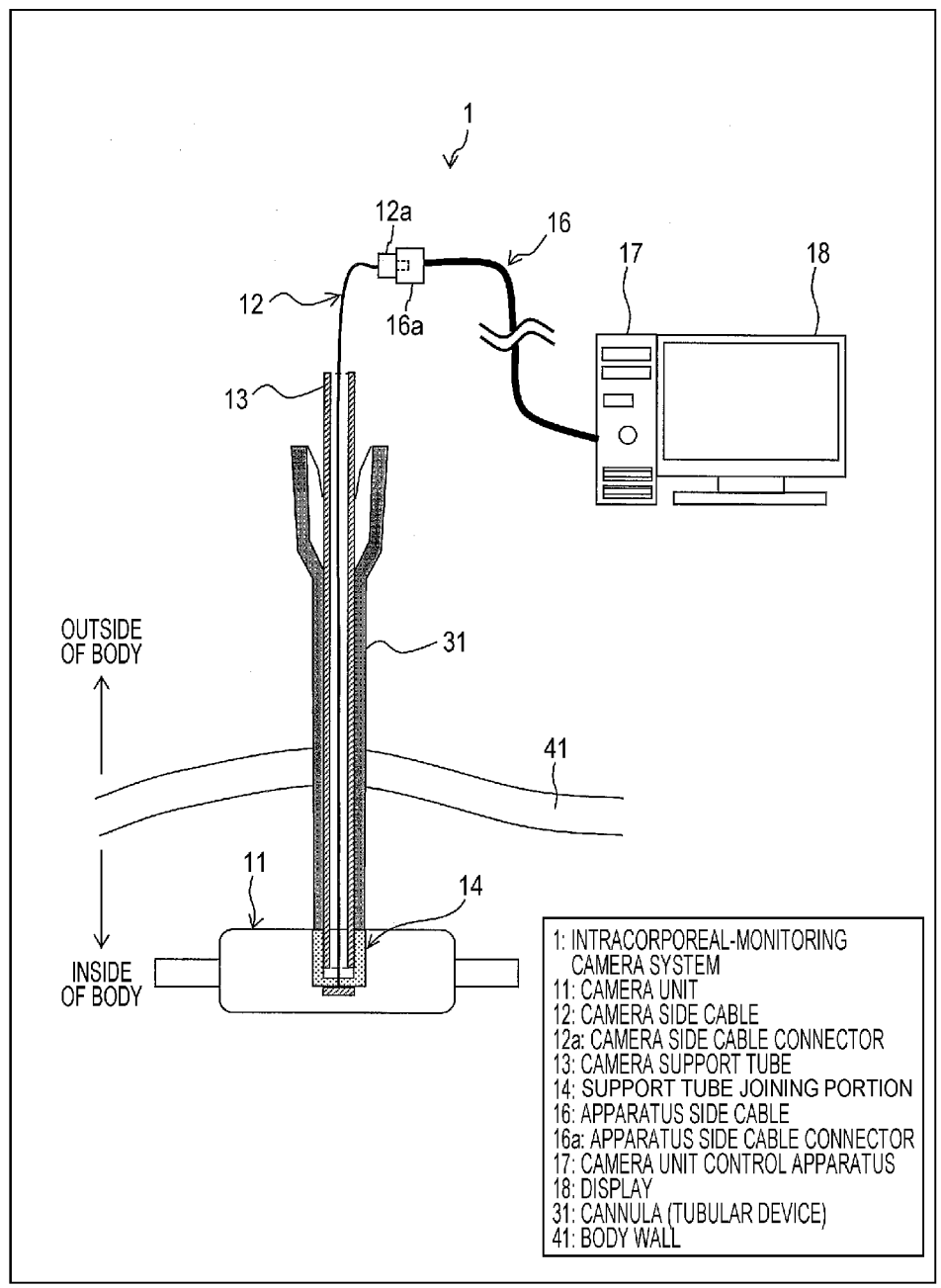
FIG. 1 is a schematic diagram that illustrates a configuration of an intracorporeal-monitoring camera system according to a first embodiment.

One embodiment of the present invention will be described below based on FIGS. 1 to 15. For convenience of description, the same reference characters will be given to members that have the same functions as the members described in the embodiments, and descriptions thereof will appropriately be omitted. Further, shapes and dimensions such as lengths, sizes, and widths of configurations illustrated in the drawings do not reflect actual shapes and dimensions but are appropriately changed for clarity and simplicity of the drawings.

First Embodiment (Configuration of Intracorporeal-Monitoring Camera System)

FIG. 1 is a schematic diagram that illustrates a configuration of an intracorporeal-monitoring camera system of a first embodiment. As illustrated in FIG. 1, an intracorporeal-monitoring camera system 1 includes a camera unit 11 (imaging portion), a camera side cable 12 whose one end is connected with the camera unit 11, a camera support tube 13 (support tube), a control system that includes a camera unit control apparatus 17 and a display 18 (display device), and an apparatus side cable 16 whose one end is connected with the camera unit control apparatus 17. A camera side cable connector 12*a* that is provided at the other end of the camera side cable 12 and an apparatus side cable connector 16*a* that is provided at the other end of the apparatus side cable 16 are fit together, and the camera unit 11 and a control system 3 are electrically connected together. In the description made below, the camera side cable connector 12*a* and the apparatus side cable connector 16*a* may be abbreviated as connector 12*a* and connector 16*a*, respectively.

One end of the camera support tube 13 is introduced in a body through an internal portion of a cannula 31 (holding tube) that is punctured through an abdominal wall. The camera unit 11 performs intracorporeal photography and is introduced in the body through a tubular member, which is referred to as trocar. A slit is provided from one end to the other end of the camera support tube 13. One end (on the inside of the body) of the camera support tube 13 and the camera unit 11 in the body are joined together in a support tube joining portion 14 (joining portion) in a state where the camera side cable 12 is placed from the slit and through the internal portion of the camera support tube 13.

In FIG. 1, a pin portion of a male type (protrusion type) camera side cable connector 12*a* is inserted in a female type (recess type) apparatus side cable connector 16*a*, and the connectors 12*a* and 16*a* are fit together. However, the male type and the female type may be reversed, and a configuration is possible in which a female type camera side cable connector and a male type apparatus side cable connector are fit together. Because the female type (recess type) camera side cable connector does not have the pin portion of the male type that is exposed to the outside, dirt is less likely to attach to a terminal portion in a case of accidental contact with an internal portion of the body. Thus, the female type (recess type) connector is preferably used for the camera side cable.

Although details will be described later, in a case where the camera unit 11 and the camera support tube 13 are connected together, the camera side cable 12 is drawn out from the inside of the body to the outside of the body through the camera support tube 13. Thus, the outer diameter of the camera side cable 12 is smaller than the outer diameter of the camera support tube 13. Thus, the outer diameter of the camera support tube 13 may be reduced by reducing the outer diameter of the camera side cable 12. This provides a significant effect of improving minimal invasiveness. That is, the outer diameter of the camera side cable 12 is preferably reduced as much as possible. For example, as illustrated in FIG. 1, the outer diameter of the camera side cable 12 is preferably made smaller than the outer diameter of the apparatus side cable 16.

In FIG. 1, for easy understanding of the drawing, the outer diameter of the camera side cable 12 is illustrated smaller than the actual outer diameter. Further, the outer diameter of the camera side cable connector 12*a* is approximately the same as the outer diameter of the camera support tube 13 and is smaller than the inner diameter of the cannula 31 (holding tube), the internal portion of which the camera side cable connector 12*a* passes through. In addition, although one pin is illustrated with the camera side cable connector 12*a* for simplicity, the camera side cable connector 12*a* is configured with the number of pins that corresponds to the number of power lines used for the cable. Those also apply to the other drawings.

As described later, the camera side cable 12 (including the camera side cable connector 12*a*) is temporarily brought back into the body when the camera unit 11 is collected. Thus, the apparatus side cable connector 16*a* of the apparatus side cable 16, which contacts with the camera side cable 12, and a portion in a prescribed length therefrom have to be maintained clean.

The above-described connection allows pictures photographed by the camera unit 11 to be transmitted to the camera unit control apparatus 17 and allows control signals from the camera unit control apparatus 17 to be transmitted to the camera unit 11.

The above-described system configuration is used, and a wired scheme is thereby employed for transmission from the camera unit 11 to the camera unit control apparatus 17. Thus, the transmission rate may be increased, and high resolution images may be obtained because signals may stably be transmitted and received. Further, communication may be performed with low power compared to a wireless scheme, and size reduction of the camera unit 11 may be expected by supplying a power source from the outside. Accordingly, a wound for introduction of the camera unit 11 in the body may be made smaller by the size reduction, thus providing a significant effect of improving minimal invasiveness.

The camera unit control apparatus 17 causes the display 18 to display the picture transmitted from the camera unit 11 and transmits the control signals to the camera unit 11. The camera unit control apparatus 17 and the display 18 may be formed integrally or separately.

(Configurations of Camera Unit and Camera Side Cable)

Figure 2:
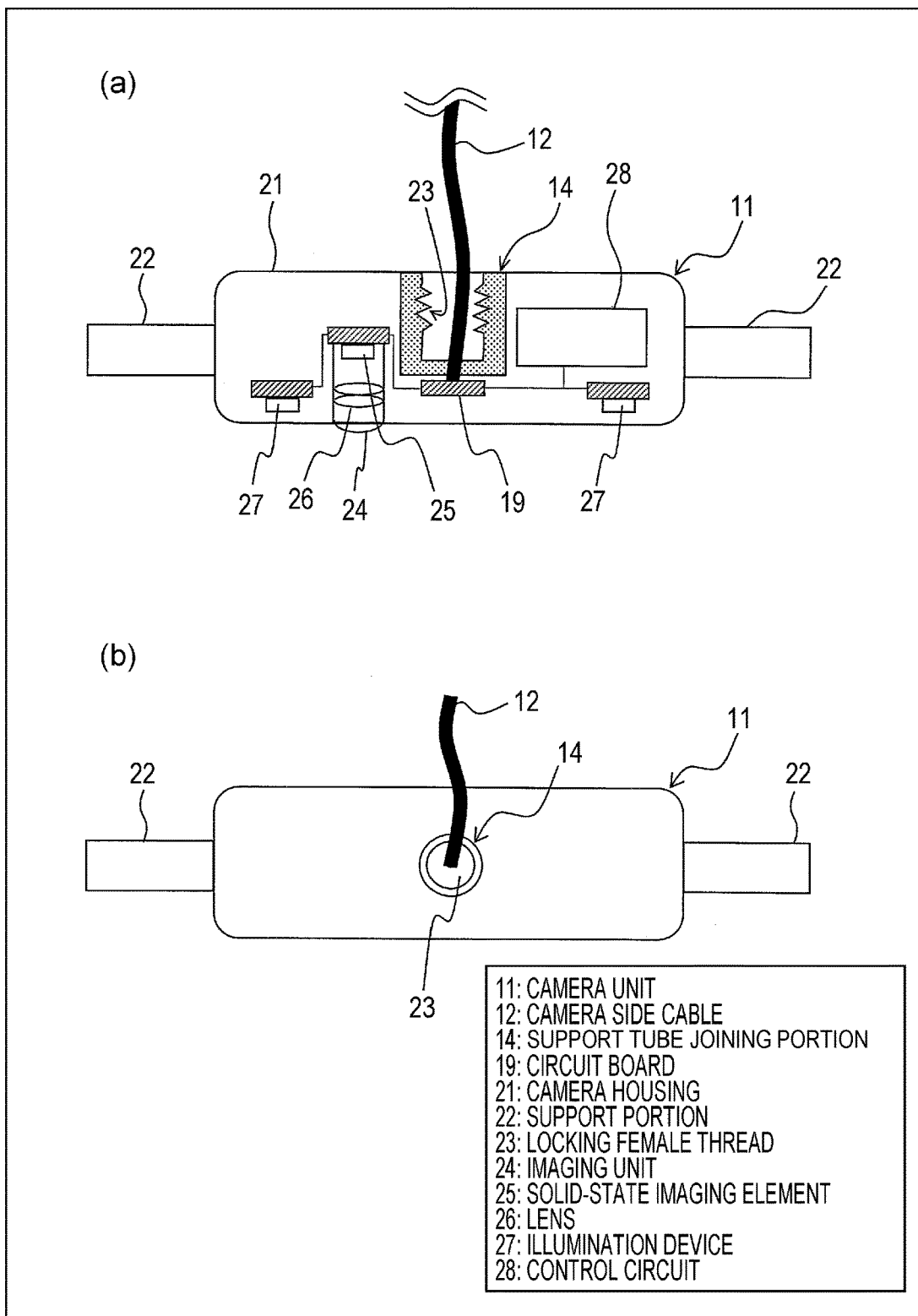
FIG. 2(a) is a schematic cross-sectional view of a camera unit according to the first embodiment.
FIG. 2(b) is a top view thereof.

FIG. 2(*a*) is a schematic cross-sectional view of a camera unit of the first embodiment, and FIG. 2(*b*) is a top view thereof. As illustrated in FIGS. 2(*a*) and (*b*), in the camera unit 11, a circuit board 19, a solid-state imaging element 25, a control circuit 28, and an illumination device 27 that are connected with the circuit board 19, and a lens 26 are provided in a camera housing 21. A recess-shaped support tube joining portion 14 is provided on an upper surface of the camera housing 21. The support tube joining portion 14 is a hole structure with a circular opening, on an inner wall of which a locking female thread 23 is provided. Further, support portions 22 protrude from both side surfaces of the camera housing 21 that are opposed to each other. The support portion 22 is gripped when the camera unit 11 is introduced in the body by using forceps and gripped such that an upper surface (a surface on which the support tube joining portion 14 is provided) of the camera unit 11 faces the end of the camera support tube 13 when the camera unit 11 and the camera support tube 13 are joined together.

The camera side cable 12 is connected with the circuit board 19 and is guided to the outside of the camera unit 11 while passing through an internal portion of the support tube joining portion 14. A connecting portion between the circuit board 19 and the camera side cable 12 are sealed by a resin or the like. In addition, the camera side cable 12 is bonded and fixed to the support tube joining portion 14 in a portion (a bottom portion of the recess-shaped support tube joining portion 14) from which the camera side cable 12 is drawn out in the internal portion of the support tube joining portion 14. One example of the bonding and fixing is sealing and fixing by an adhesive or an O-ring. Permeation of water, entrance of foreign objects, and so forth from the bonded and fixed portion into the camera unit 11 are inhibited.

Further, as described later, because the camera side cable 12 is introduced in the body cavity through a tubular member such as the trocar and drawn out to the outside of the body through the camera support tube 13 while being connected with the camera unit 11, the camera side cable 12 is formed of a flexible material with flexibility.

As the solid-state imaging element 25, a CCD (charge coupled device), a CMOS (complementary metal-oxide semiconductor) image sensor, and so forth are used, for example. The solid-state imaging element 25 and the lens 26 configure an imaging unit 24.

The illumination device 27 illuminates internal portions of the body and thereby makes pictures photographed by the camera unit 11 clear. The illumination device 27 is preferably of a small size, and an LED (light emitting diode) and so forth may preferably be used, for example. As illustrated in FIG. 2, plural illumination devices 27 may be installed in the camera unit 11.

Further, in the camera housing 21 of the camera unit 11, portions in which the lens 26 and the illumination device 27 are arranged are configured with a transparent material, but other regions may be configured with materials in blue, bluish green, and green of cold colors, which are easy to recognize in internal portions of the body. Further, a film on a surface of the camera side cable 12 is further preferably configured with a blue, bluish green, or green material. In addition, the cable connector is preferably configured with a similarly colored material. As described above, blue, bluish green, and green of cold colors in the complementary color relationship with colors of internal portions of the body such as red and yellow are used, thereby increasing visibility in installation work and collection work in the body, which will be described later. For example, in a case where the camera unit 11 is accidentally dropped in the body and placed behind an organ, because the camera side cable 12 is long compared to the camera unit 11, the camera side cable 12 is likely to be seen in a visible place and is easy to find immediately. Thus, coloring the camera side cable 12 in blue, bluish green, or green provides significant effects such as reduction in time of the installation work of the camera unit 11 and enhanced safety. As described above, colors that correspond to visible light at wavelengths of 420 to 570 nm (colors easy to recognize in the body) may be used for coloring of the camera unit 11 and the camera side cable 12.

Further, easily visible phosphorescent materials and reflective materials may be used other than coloring with blue or green materials as described above. Such configurations allow the camera unit 11 and the camera side cable 12 to be immediately found in a case where those are present in a portion behind an organ, which is not very visible, or at the edge of the visible field, which illumination light is not likely to cover, and are thus particularly effective.

(Structures of Camera Support Tube and Cannula)

Figure 3:
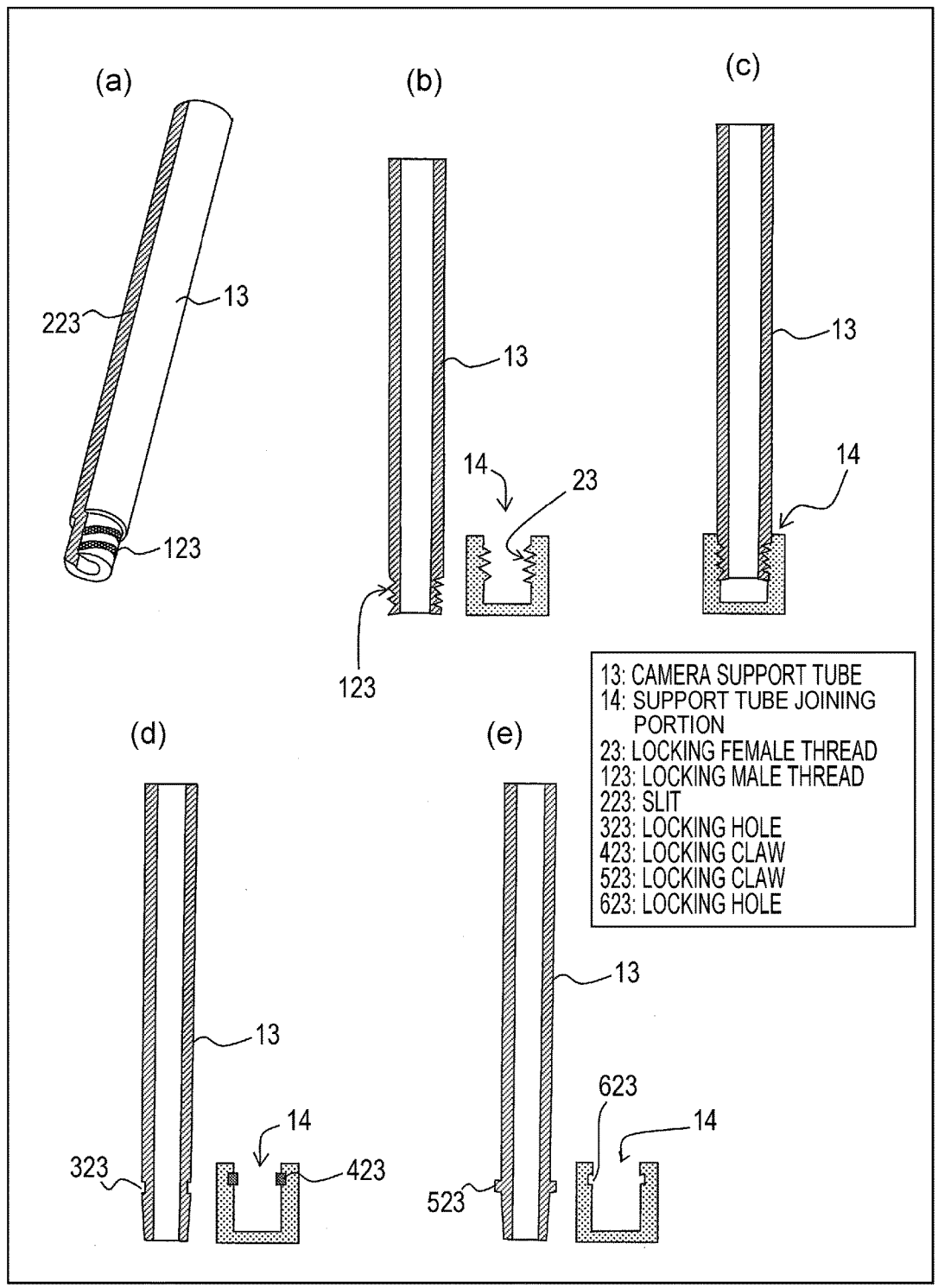
FIG. 3(a) is a perspective view of a camera support tube of FIG. 1.
FIG. 3(b) is a cross-sectional view of the camera support tube and a support tube joining portion of FIG. 1.
FIG. 3(c) is a cross-sectional view that illustrates a joining state between the camera support tube and the support tube joining portion of FIG. 1.
FIGS. 3(d) and (e) are cross-sectional views that illustrate modification examples of the camera support tube and the support tube joining portion.
Figure 4:
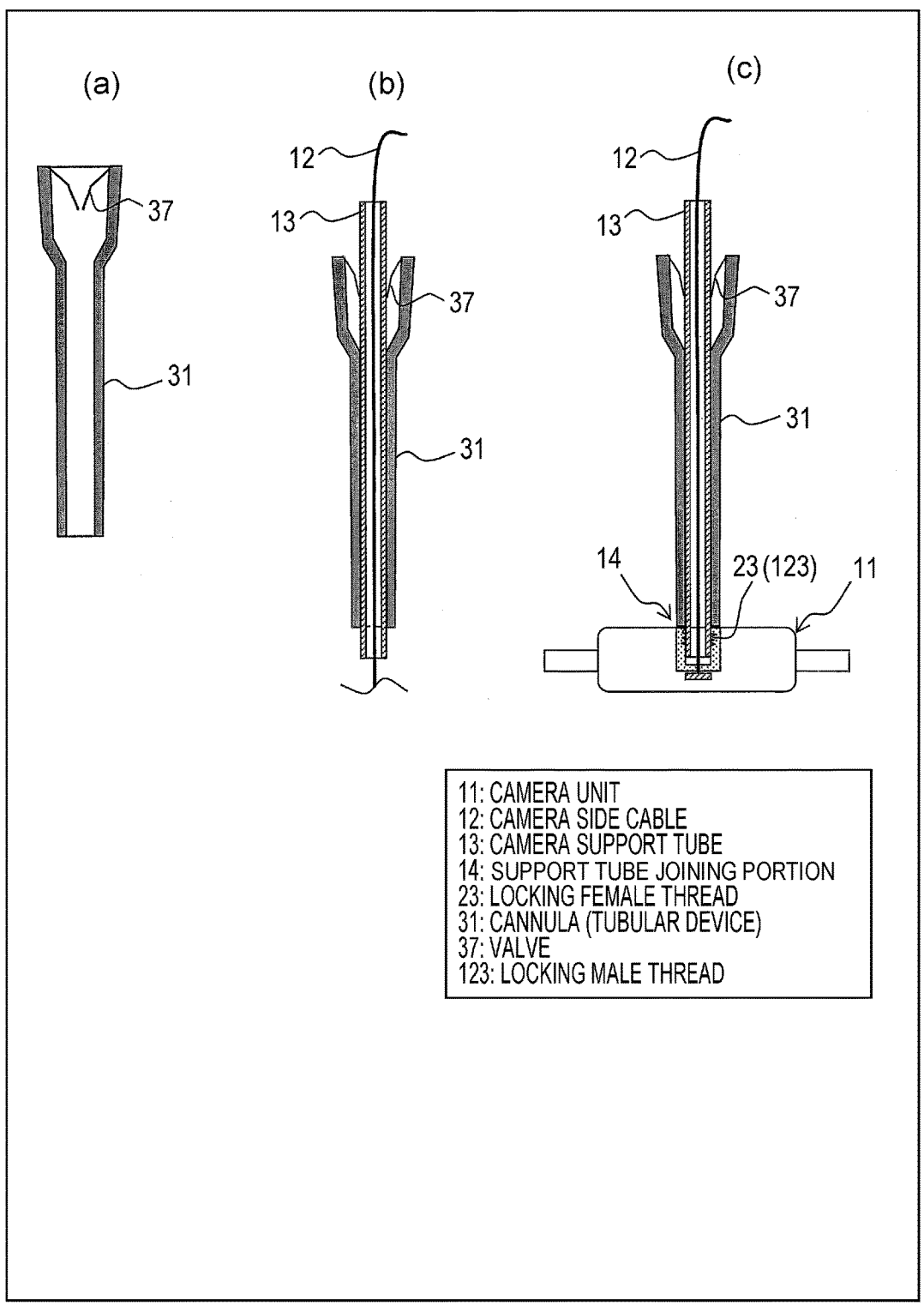
FIG. 4(a) is a cross-sectional view that illustrates a structure of a cannula.
FIG. 4(b) is a cross-sectional view that illustrates a state where the camera support tube of FIG. 3 is inserted in the cannula of FIG. 4(a)
FIG. 4(c) is a cross-sectional view that illustrates a joining state between the camera support tube inserted in the cannula and the camera unit of FIG. 2.

FIG. 3 illustrates outline structures of the camera support tube 13 and the support tube joining portion 14. FIG. 3(*a*) is a perspective view of the camera support tube 13. The camera support tube 13 is a support tube, which is joined to the camera unit 11 in the body in a state where the camera side cable 12 is drawn out to the outside of the body through an internal portion of the camera support tube 13 and thereby supports the camera unit 11. One end of the camera support tube 13 is introduced in the body through a body wall 41 such as the abdominal wall. The end introduced in the body is joined to the camera unit 11 at the support tube joining portion 14.

As illustrated in FIG. 3(*a*), the camera support tube 13 is a structure, in which a linear slit 223 that is provided from one opening (on the inside of the body) to the other opening (on the outside of the body) along an axis of the camera support tube 13 is provided on a side surface of a cylindrical tube, and has a locking male thread 123 at an end on the side introduced in the body. The width of the slit 223 is larger than the diameter of the camera side cable 12 (at least larger than the minor axis of the cross section of the cable).

In view of the joining strength to the camera unit 11, the camera support tube 13 is formed of a hard material. Materials of the camera support tube 13 are not particularly limited as long as the materials have the joining strength that may stably support the camera unit 11 and have rigidity that may fix the camera unit 11 in desired position and direction. Examples may include stainless steel, ceramics (fine ceramics), reinforced plastic, and so forth.

The camera support tube 13 has a cylindrical shape and is thus easily combined with a common cannula, which is similarly a tube having a cylindrical shape. The camera support tube 13 may also be used as a puncture instrument by sharpening a tip or cutting the tip into an obliquely round shape like an injection needle.

Further, the width of most of the slit 223 is larger than the diameter of the camera side cable 12 as illustrated in FIG. 12(a), but the width of a portion may be smaller than the diameter of the camera side cable 12 as illustrated in FIG. 12(b). FIG. 13(a) is a perspective view of the end of the camera support tube, and FIG. 13(b) is a cross-sectional view that includes the slit of the camera support tube. As illustrated in FIGS. 13(a) and (b), as for both ends of the camera support tube 13, plural paired protrusions 255 that face each other are formed on both edges of the slit 223. Accordingly, the width of a portion 223p of the slit that corresponds to the paired protrusions 255 becomes smaller than the cable diameter, the camera side cable 12 may be placed through the portion 223p of the slit while being temporarily elastically deformed when the camera side cable 12 is placed through the camera support tube 13 (see FIG. 12(c)), and the diameter of the camera side cable 12 recovers after placement through the camera support tube 13 (see FIG. 12(b)). This restrains the camera side cable 12 from being easily removed from the camera support tube 13 and significantly improves working efficiency in installation of the camera support tube 13. As illustrated in FIG. 14, a similar effect may be obtained by forming only one pair of paired protrusions 255 at each of both ends (tip end and tail end of the slit) of the camera support tube 13.

Figure 13:
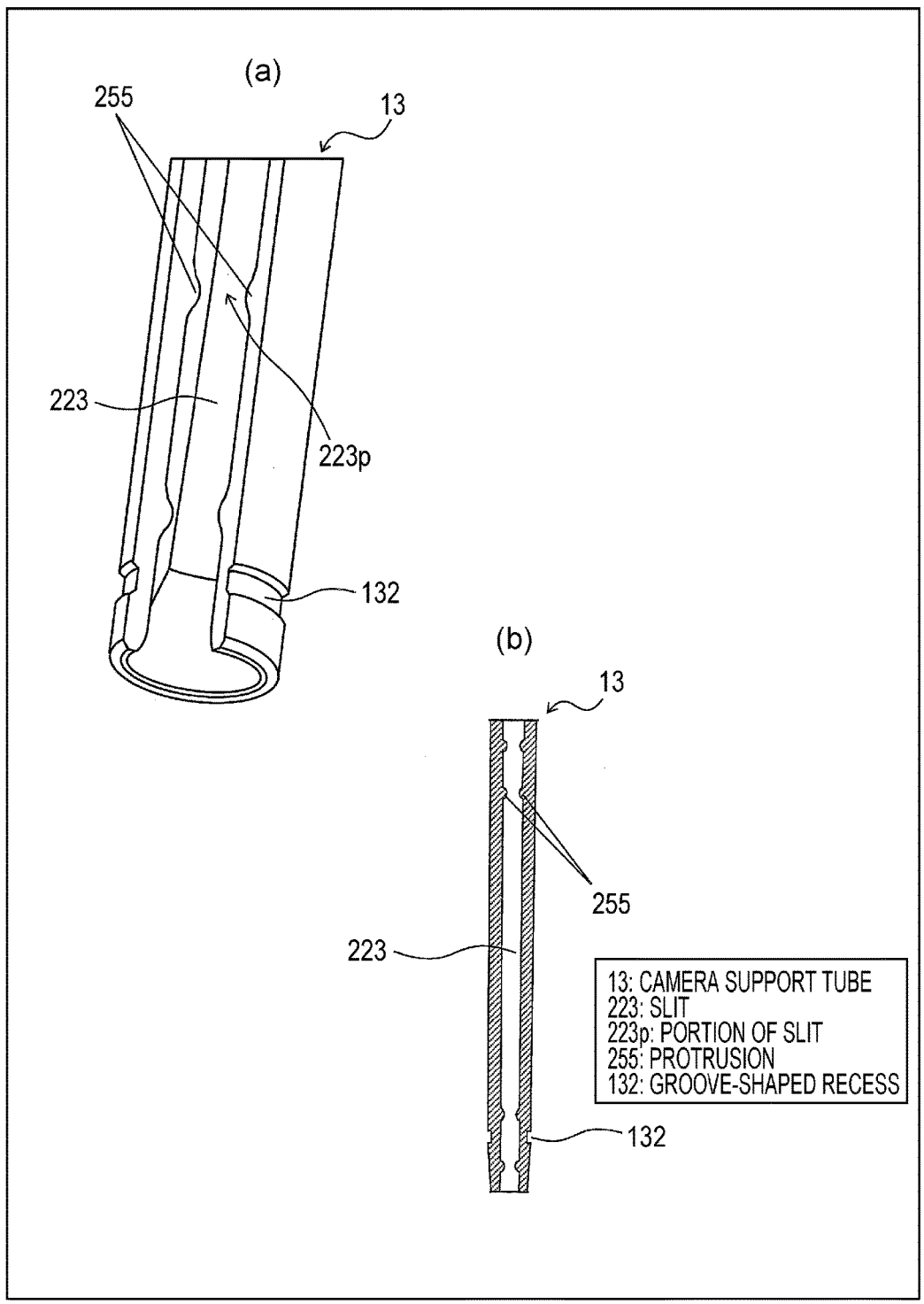
FIG. 13(*a*) is a perspective view that illustrates a configuration example of an end of the camera support tube, and FIG. 13(*b*) is a cross-sectional view that includes the slit of the camera support tube.
Figure 14:
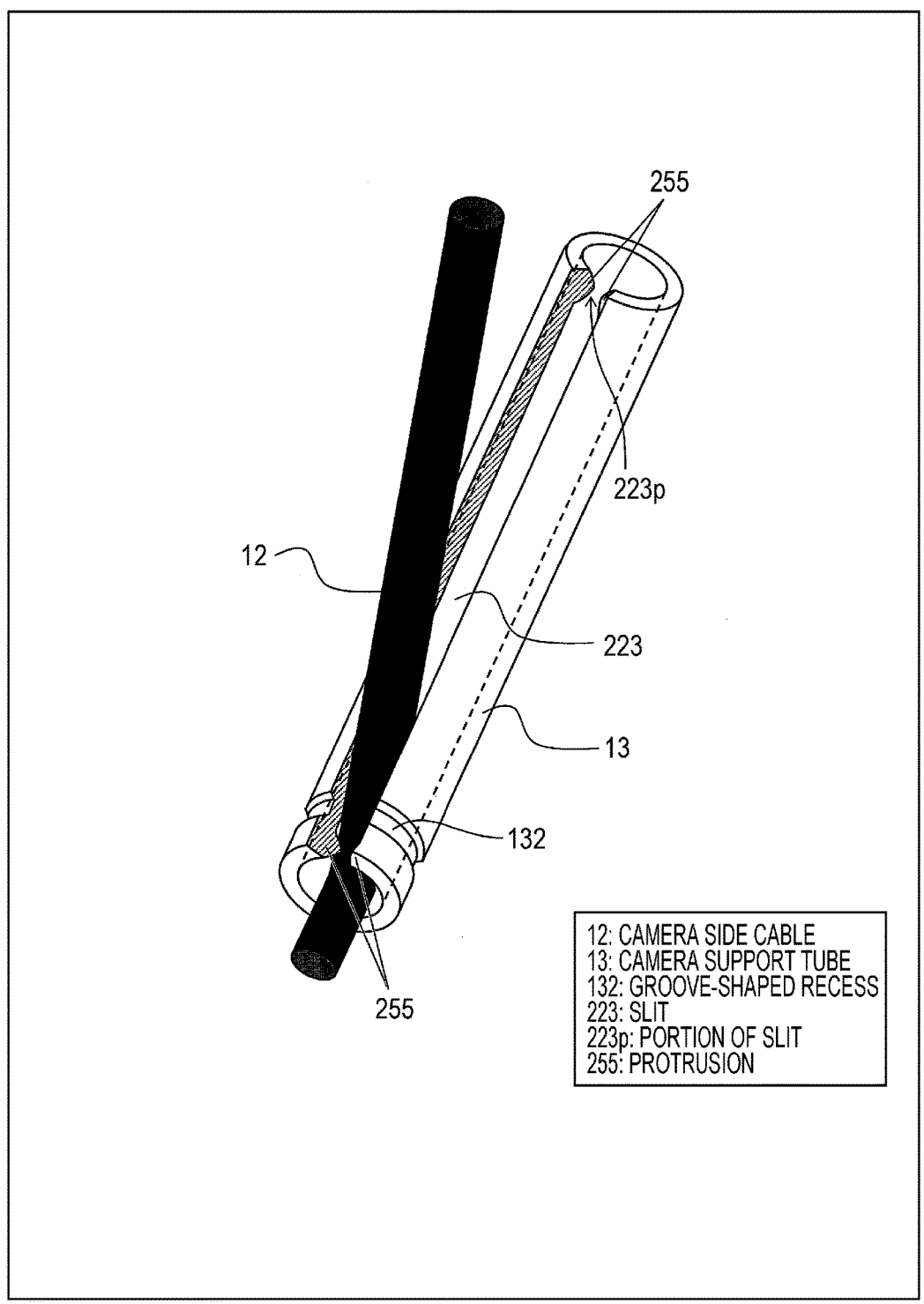
FIG. 14 is a perspective view that illustrates a state where the camera side cable is placed through the camera support tube.

In FIGS. 13 and 14, the paired protrusions 255 are formed on both sides of the portion 223p of the slit 223. However, embodiments are not limited to this. A configuration is possible in which a protrusion is provided on one side of a portion of the slit 223 and the width of the portion of the slit 223 is thereby made smaller than the diameter of the camera side cable 12.

FIG. 3(b) is a cross-sectional view of the camera support tube 13 and the support tube joining portion 14, and FIG. 3(c) is a cross-sectional view that illustrates a state where the camera support tube 13 is inserted in the support tube joining portion 14. As illustrated in FIGS. 3(b) and (c), the camera support tube 13 is formed such that the locking male thread 123 fits in the locking female thread 23. The camera support tube 13 is not limited to the above structure. For example, as illustrated in FIGS. 3(d) and (e), a tip portion may be a taper shape (narrowing shape).

As described above, in a case where the tip portion of the camera support tube 13 is formed into a taper shape (narrowing shape) to facilitate insertion of the camera support tube 13, the narrowing shape may be formed by thinning the wall thickness of the camera support tube 13. In this case, it is further preferable that the camera support tube 13 is configured to have a regular inner diameter and only the outer diameter is changed (the external shape is reduced toward the tip), because a case where an instrument is caught and may not pass through at an intermediate portion (narrow part) in insertion of the instrument in the internal portion of the camera support tube is avoided.

As illustrated in FIG. 3(d), a locking hole 323 may be provided in the camera support tube 13, and a locking claw 423 may be provided in the support tube joining portion 14. Further, as illustrated in FIG. 3(e), a locking claw 523 may be provided in the camera support tube 13, and a locking hole 623 may be provided in the support tube joining portion 14.

Further, a groove-shaped recess 132 that is formed around an outside surface as illustrated in FIGS. 13(a) and (b) may be provided at the end of the camera support tube 13. Correspondingly, a ridge-shaped protrusion that is formed around an inside surface of the support tube joining portion 14 may be provided. Further, a ridge-shaped protrusion that is formed around the outside surface may be provided at the end of the camera support tube 13. Correspondingly, a groove-shaped recess that is formed around the inside surface of the support tube joining portion 14 may be provided. This is further preferable because an operation for matching positions of the locking hole and the locking claw does not have to be performed in insertion of the camera support tube 13, joining between both of those is facilitated, and the fitting strength is increased.

Further, each of the camera support tube 13 and a support tube joining portion 14 may be configured with plural materials. For example, the above locking claw 423 and the locking claw 523 may be configured with elastic materials such as resins. That is, at least one of a support tube recess and a joining portion protrusion may be configured with elastic materials such as resins, and the other may be configured with hard materials such as metal.

In such a configuration, the elastic material passes through a slightly narrow part in which the locking claw 423 (elastic material) of a joining portion is arranged, while being deformed. After passing, the elastic material recovers the original shape by elastic force and is firmly fit, thus improving the joining strength. Embodiments are not limited to this example, but an elastic material may be formed in at least one of the recess and protrusion of the support tube and joining portion.

Further, in such a configuration, a hand may sense a fitting action, and the operator who is operating the fitting may sense a reaction of the fitting and recognize that the fitting is made. This results in an advantage of avoiding excessive and continuous application of force.

Further, heat dissipation from the camera unit 11 is enhanced by forming side surfaces of the camera support tube 13 and the support tube joining portion 14 with materials with high heat conductivity. An elastic material is used only for the protrusion of the support tube joining portion 14, the joining strength is thereby enhanced, and a function of providing the reaction of the fitting is thereby added. As described above, a configuration with plural materials with different properties enables plural kinds of desired performance such as joining performance and heat dissipation to be simultaneously realized.

Embodiments are not limited to a configuration example in the above example, but the combination of those materials may be reversed. That is, the locking claw may be configured with hard materials such as metal, and a portion that includes the locking hole may be configured with elastic materials such as resins.

Figure 15:
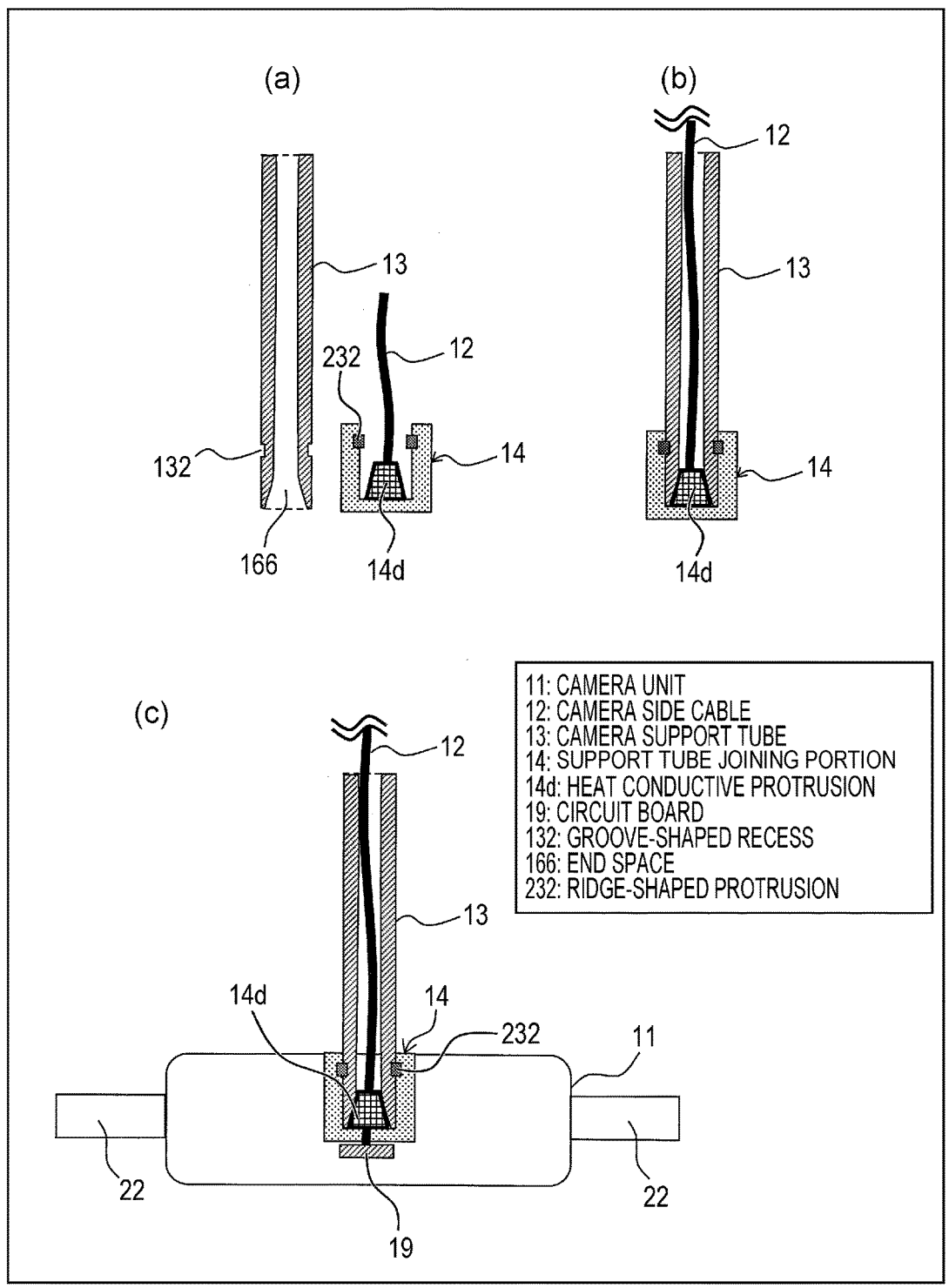
FIG. 15(*a*) is a cross-sectional view that illustrates modification examples of the camera support tube and the support tube joining portion, FIG. 15(*b*) is a cross-sectional view that illustrates a state where the camera support tube is inserted in the support tube joining portion, and FIG. 15(*c*) is a cross-sectional view that illustrates a joining state between the camera support tube and the camera unit.

FIG. 15 illustrates one example of the above-described configuration in which joining performance and heat dissipation are enhanced. FIG. 15(a) is a cross-sectional view of the camera support tube 13 and the support tube joining portion 14, and FIG. 15(b) is a cross-sectional view that illustrates a state where the camera support tube 13 is inserted in the support tube joining portion 14. Further, FIG. 15(c) is a cross-sectional view that illustrates a joining state between the camera support tube 13 and the camera unit 11 illustrated in FIG. 2.

As illustrated in FIGS. 15(a) and (b), the groove-shaped recess 132 that is formed around the outside surface is provided at the end of the camera support tube 13 on the inside of the body. Correspondingly, a ridge-shaped protrusion 232 that is formed around the inside surface of the recess-shaped support tube joining portion 14 is provided.

In addition, a heat conductive protrusion 14d that is formed of a highly heat conductive metal material, for example, is provided at the bottom of the recess-shaped support tube joining portion 14, and the camera side cable 12 is bonded and fixed to an internal portion of the heat conductive protrusion 14d. In this case, the camera side cable 12 is drawn out from the heat conductive protrusion 14d of the support tube joining portion 14. One example of the bonding and fixing is sealing and fixing by crimping, an adhesive, or an O-ring. Accordingly, permeation of water, entrance of foreign objects, and so forth from the bonded and fixed portion into the camera unit 11 are inhibited.

More specifically, the heat conductive protrusion 14d is in a truncated conical shape that narrows toward an opening portion (entrance portion) of the support tube joining portion 14, the camera side cable 12 is placed through a hole formed in the axial direction of the heat conductive protrusion 14d, and the camera side cable 12 is bonded and fixed to the heat conductive protrusion 14d in the hole. As for the end (on the inside of the body) of the camera support tube 13 that is joined to the support tube joining portion 14, an internal portion (end space 166) of the end is formed in an inverted taper shape (a shape whose inner diameter becomes larger toward a tip) that corresponds to the truncated conical shape of the heat conductive protrusion 14d. Accordingly, when the camera support tube 13 is joined by using the camera side cable 12 as a guide, the end space 166 in the inverted taper shape of the camera support tube 13 is guided to the heat conductive protrusion 14d of the support tube joining portion 14, thus facilitating insertion of the camera support tube 13.

Further, when the camera support tube 13 is fit in the support tube joining portion 14, an outer peripheral surface of the end of the camera support tube 13 contacts with an inside wall of the support tube joining portion 14, and an inner peripheral surface of the end of the camera support tube 13 contacts with the heat conductive protrusion 14d of the support tube joining portion 14. This provides significant effects such as enhancing the joining performance between both of those and further improving heat dissipation of the heat transmitted from the camera unit 11 to the camera support tube 13.

In a case where the end space 166 of a camera support tube 13 is formed into the inverted taper shape, it is preferable that the camera support tube 13 is configured to have a regular outer diameter or have a slightly narrowing shape, the wall thickness of the camera support tube 13 is thinned toward the tip, and the outer diameter of the camera support tube 13 thereby does not become large. Accordingly, a case may be avoided where the camera support tube 13 is caught by an inner wall of a tubular device and does not pass through when the camera support tube 13 is inserted in an internal portion of a tubular device such as the cannula.

Various examples have been described in the above description. However, it is matter of course that configuration materials of such support tube and joining portion may similarly be used in plural combinations in other embodiments.

FIG. 4(a) is a cross-sectional view of the cannula, FIG. 4(b) is a cross-sectional view that illustrates a state where the camera support tube 13 of FIGS. 3(a) to (e) is inserted in the cannula 31 illustrated in FIG. 4(a), and FIG. 4(c) is a cross-sectional view that illustrates a joining state between the camera support tube 13 inserted in the cannula 31 and the camera unit 11 illustrated in FIG. 2.

As illustrated in FIG. 4(a), the cannula 31 is a tubular device, one end (on the outside of the body) is thicker than the other end (on the inside of the body), and the one end (on the outside of the body) functions as a stopper when the cannula 31 is inserted in the body wall 41. This restrains the camera support tube 13 from falling into the body and enables the cannula 31 to be fixed to the body wall 41.

Further, the cannula 31 is a structure in which a valve 37 with restorability is provided in an internal portion of the one end (on the outside of the body). A valve structure that may be expanded when external force is applied in the direction from the thick end (on the outside of the body) to the narrow end (on the inside of the body) is provided in a central portion of the valve 37.

The cannula 31 preferably has a small diameter in order to realize minimal invasiveness. Specifically, the cannula 31 preferably has a diameter of 3 mm or smaller.

(Insertion in Cannula and Joining to Camera Unit of Camera Support Tube)

In a case where the camera unit 11 is joined into the camera support tube 13 in the body, as illustrated in FIG. 4(b), the narrow end of the camera support tube 13 is first pressed onto the thick end (on the outside of the body) of the cannula 31 in a state where the camera side cable 12 is placed through the internal portion of the camera support tube 13, and the camera support tube 13 is inserted into the cannula 31 until the narrow end of the camera support tube 13 is exposed from the cannula 31. Here, the valve 37 is expanded by the camera support tube 13, the urging force due to the restorability tightly fastens the camera support tube 13, and the camera support tube 13 is consequently fixed to the cannula 31. The thick end (on the outside of the body) of the camera support tube 13 is also exposed from the cannula 31.

Next, as illustrated in FIG. 4(c), the camera side cable 12 is used as a guide, and the locking male thread 123 of the narrow end (on the inside of the body) of the camera support tube 13 is thereby inserted in the locking female thread 23 of the support tube joining portion 14 and fit therein by the threads. Accordingly, the locking male thread 123 is fit in the locking female thread 23, and the camera unit 11 and the camera support tube 13 are thereby joined together with high mechanical strength. The locking male thread 123 and the locking female thread 23 are not limited to thread shapes but may be in any shapes that fit together. A press-fitting structure that uses an elastic material or the like may be used instead of the locking female thread 23.

In a case where the camera support tube 13 is inserted and fit in the support tube joining portion 14 by using not a thread shape but a locking claw or the like, the strength for fitting the camera support tube 13 and the support tube joining portion 14 together is preferably configured lower than the bonding strength of a bonding-fixing portion that bonds and fixes the camera side cable 12 to the camera unit 11. This is because the camera support tube 13 has to be inserted in the support tube joining portion 14 of the camera unit 11 while the cable is held, pulled, supported, and used as a guide, and if the fitting strength between the camera support tube 13 and the support tube joining portion 14 is higher than the bonding strength of the above bonding-fixing portion, this leads to a possibility that the bonding-fixing portion is broken or the body wall of the patient is damaged due to the camera unit 11 pulled in the direction to the outside of the body.

For example, specifically, the strength for fitting the camera support tube 13 and the support tube joining portion 14 together is preferably equal to or smaller than 30 N (newton), which is smaller than the bonding strength of the bonding-fixing portion. In addition, an optimal range is preferably configured as a range of 3 to 6 N. In a case where the strength is configured in this range, fitting is made without applying excessively large force in fitting. Further, because the hand may sense the fitting action of the camera support tube 13, no excessive force is continuously applied. This provides a significant effect of safe installation.

(Using Method and Effects of Intracorporeal-Monitoring Camera System in First Embodiment)

Figure 5:
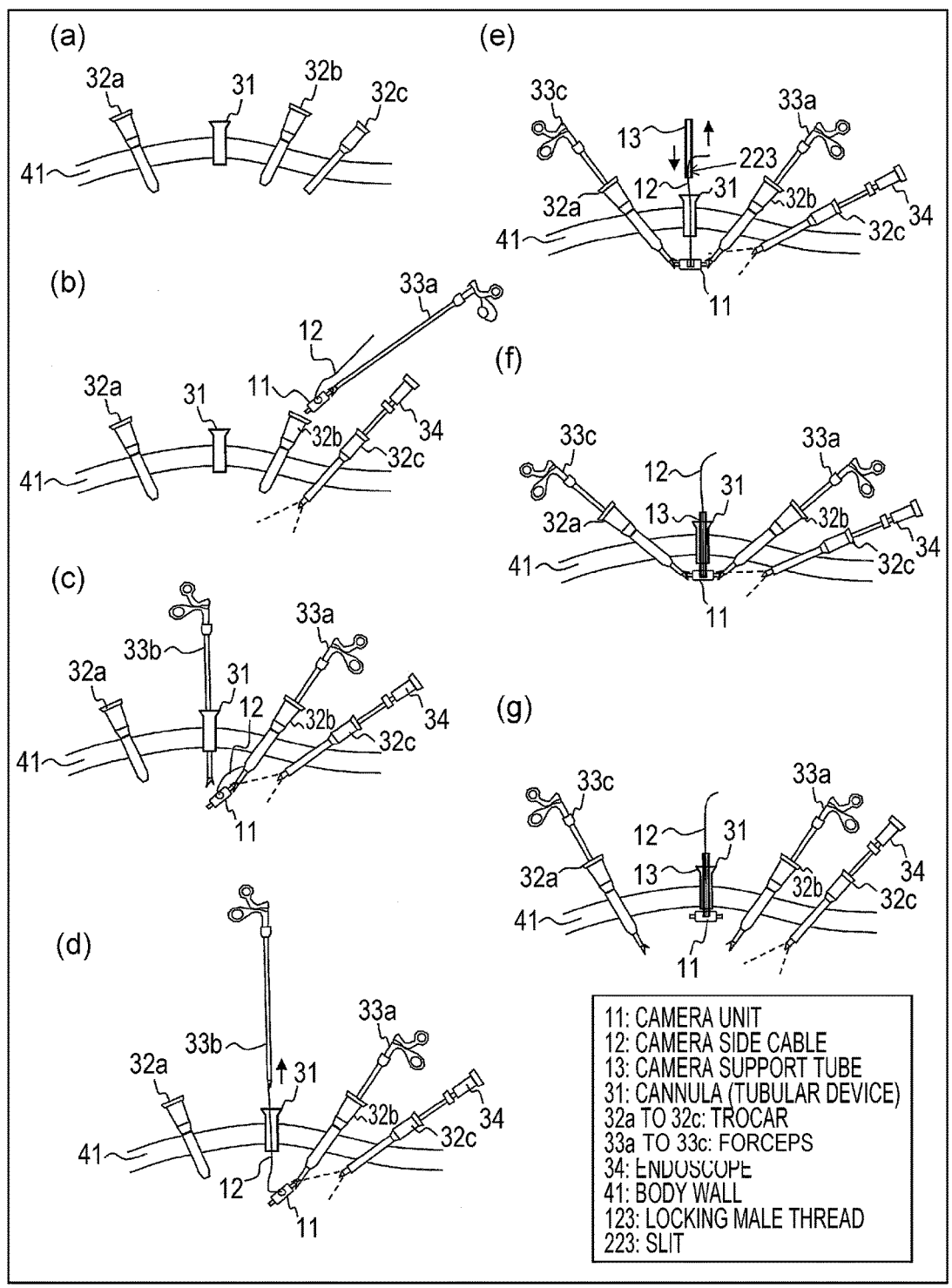
FIGS. 5(*a*) to (*g*) are schematic diagrams that illustrate a method of installing the camera unit in a body in the first embodiment.
Figure 6:
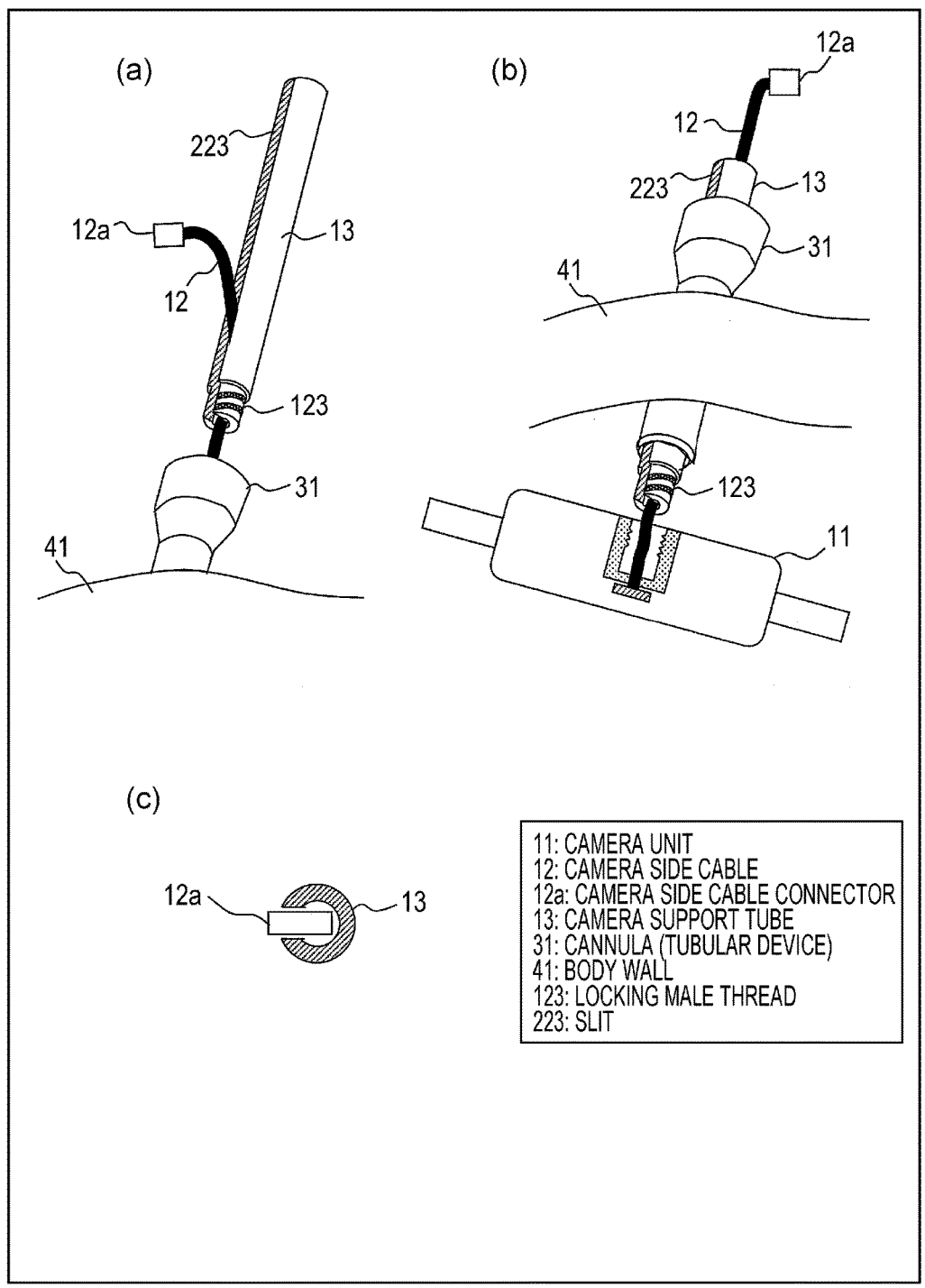
FIGS. 6(*a*) and (*b*) are perspective views that specifically illustrate FIG. 5(*e*) that is a method of installing the camera support tube of the first embodiment.

FIGS. 5(*a*) to (*g*) are schematic diagrams that illustrate a method of installing the camera unit 11 in the body in the first embodiment. FIG. 6 is a schematic diagram that illustrates a use situation of the intracorporeal-monitoring camera system in the first embodiment.

As illustrated in FIG. 5(*a*), the operator first opens a hole (port) for inserting the forceps and the endoscope in the body cavity in the body wall 41 and inserts trocars 32*a* to 32*c* in the port. In addition, in order to install the camera unit 11 in the body cavity, a port is opened in a position in the body wall 41 from which whole the organ including the affected site may be seen, and the cannula 31 is inserted therein. Specifically, while a needle-shaped obturator is placed through the internal portion of the cannula 31, the obturator is punctured into the port, and the cannula 31 is thereby inserted in the body wall 41. Further, the cannula preferably has a small diameter in order to realize minimal invasiveness. Specifically, the cannula 31 preferably has a diameter of 3 mm or smaller. After at least one of the trocars 32*a* to 32*c* and the cannula 31 is inserted, the operator sends gas into the body through the trocar, in advance inflates the body cavity, and thereby secures a space to insert instruments.

Next, as illustrated in FIG. 5(*b*), the operator inserts an endoscope 34 in the body cavity through the trocar 32*c* and inserts the camera unit 11 gripped by forceps 33*a* in the body cavity through the trocar 32*b* while observing the internal portion of the body by using the endoscope 34.

Next, as illustrated in FIG. 5(*c*), the operator moves the camera unit 11 to a vicinity of the cannula 31 by operating the forceps 33*a* and inserts forceps 33*b* in the body cavity through the cannula 31.

Next, as illustrated in FIG. 5(*d*), the operator pulls out the forceps 33*b* from the cannula 31 in a state where the camera side cable 12 is pinched by the forceps 33*b* and thereby guides the camera side cable 12 to the outside of the body. Here, the camera unit 11 (the support portion 22 thereof) is gripped by the forceps 33*a*.

Next, as illustrated in FIG. 5(*e*), the operator inserts forceps 33*c* in the body cavity through the trocar 32*a*, keeps gripping the support portions 22 on both the sides of the camera unit 11 by two pairs of forceps 33*a* and 33*c* such that the support tube joining portion 14 becomes parallel and close to an opening of the cannula 31, places the camera side cable 12 guided to the outside of the body in the internal portion of the camera support tube 13 through the slit 223 in a side surface of the camera support tube 13, and inserts the camera support tube 13 in the cannula 31. When the camera side cable 12 is placed through the camera support tube 13 in work of FIG. 5(*e*), a portion of the camera side cable 12 is inserted along the slit 223 of the camera support tube 13. In this state, the camera side cable 12 is pulled upward, and the camera support tube 13 is simultaneously inserted in the cannula 31.

Here, because the camera side cable 12 may be inserted in the internal portion of the camera support tube through the slit 223, insertion work of the camera support tube 13 in the body becomes very simple. Further, the slit 223 reduces restriction of length of the camera side cable 12. In a case where the slit 223 is not provided, the camera side cable 12 has to have at least the length that corresponds to the total length of the cannula 31 and the camera support tube 13. However, in a case where the slit 223 is provided, it is sufficient that the camera side cable 12 is longer than the length of the cannula 31. That is, as illustrated in FIGS. 6(*a*) and (*b*), after the camera side cable 12 is pulled up through the cannula 31, the camera support tube 13 is inserted in the cannula 31 such that the slit 223 is along the camera side cable 12 in a state where a portion of the camera side cable 12 is placed through a lower portion of the slit 223 of the camera support tube 13, and the camera support tube 13 is thereby connected with the camera unit 11 in the body.

Further, the slit 223 is provided, and the external dimension of the camera side cable connector 12*a* connected with the camera side cable 12 may thereby be made larger than the inner diameter of the camera support tube 13 as illustrated in FIG. 6(*c*). Thus, the connection of the camera side cable connector 12*a* with the apparatus side cable connector 16*a* is facilitated, and work efficiency may be increased. Further, the external dimension of the camera side cable connector 12*a* is made smaller than the inner diameter of the cannula 31.

Further, as another effect than an improvement in work efficiency, the gas inflating the body cavity is gradually discharged by a small amount to the outside of the body due to the provided slit 223, an air current is generated in a part of the slit 223, and an effect of cooling the support tube may thereby be provided. This provides a significant effect of emitting heat generated by the camera unit 11 to the outside of the body. Because a temperature increase of the camera unit 11 is suppressed, a significant effect of enhancing safety is obtained.

Next, as illustrated in FIG. 5(*f*), the operator uses the camera side cable 12 as a guide to insert the end of the camera support tube 13 that is exposed from the cannula 31 in the support tube joining portion 14 of the camera unit 11 and fit the end therein together by threads and joins the camera support tube 13 and the camera unit 11 together.

In a case where the camera support tube 13 is inserted and fit in the support tube joining portion 14 by using not a thread shape but a locking claw or the like and where the camera support tube 13 is inserted in the support tube joining portion 14 of the camera unit 11, the force necessary for fitting the camera support tube 13 and the support tube joining portion 14 together (for example, 3 to 6 N) is set sufficiently smaller than the bonding strength (for example, 30 N or higher) of the bonding-fixing portion of the camera side cable 12 to the camera unit 11. Thus, the camera support tube 13 may safely be inserted and fit by pulling the camera unit 11 by using the cable as a guide.

Next, as illustrated in FIG. 5(*g*), the operator pulls up the camera support tube 13 and makes the camera unit 11 contact with the end of the cannula 31 on the inside of the body such that internal portions of the body cavity may be photographed as widely as possible. Because the camera support tube 13 is tightly fastened by the valve 37 (see FIG. 4) of the cannula 31, the camera support tube 13 and the camera unit 11 maintain this state.

Figure 7:
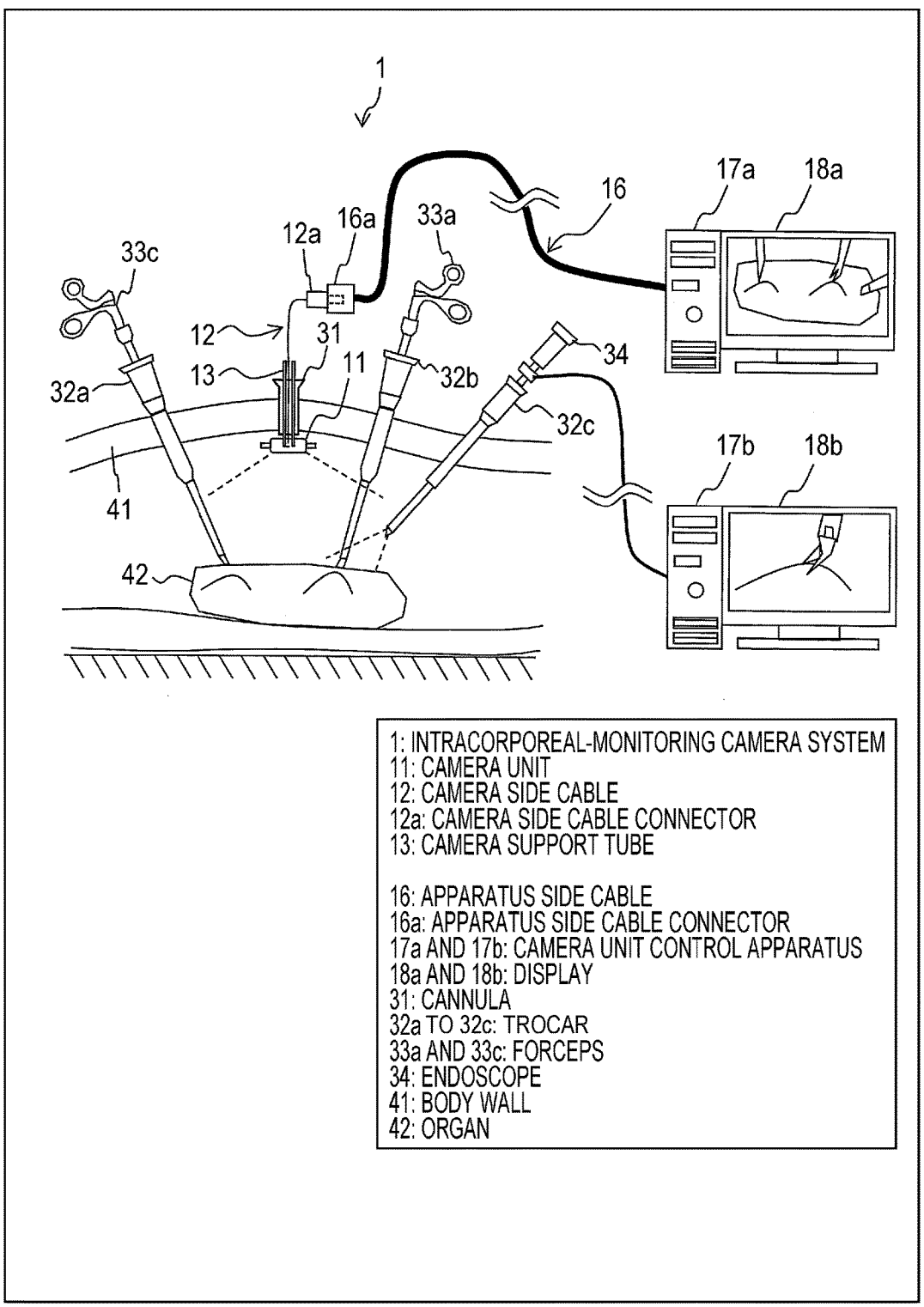
FIG. 7 is a schematic diagram that illustrates a using method of the camera unit in the first embodiment.
Figure 8:
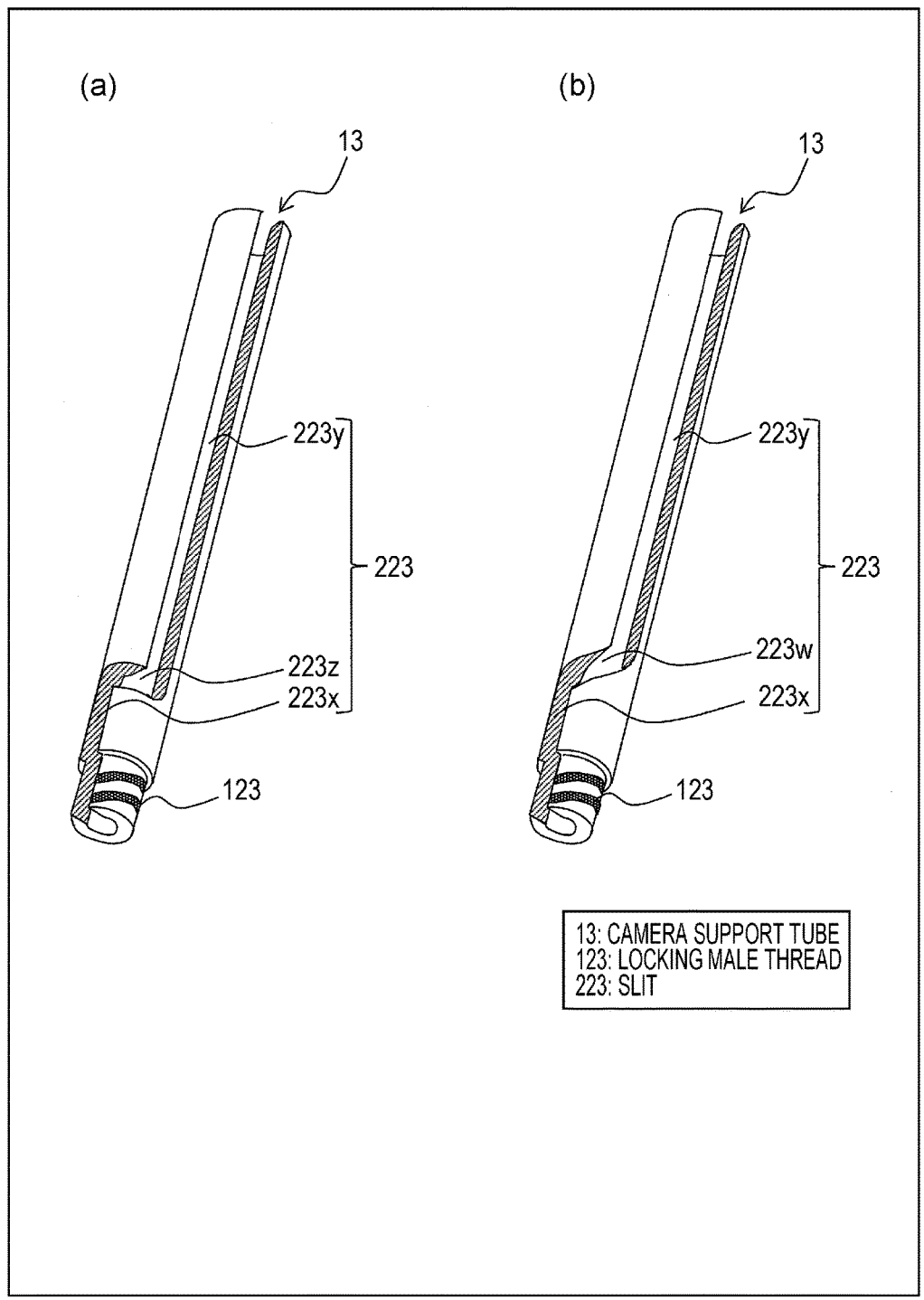
FIGS. 8(*a*) and (*b*) are perspective views of the camera support tube of a second embodiment.
Figure 9:
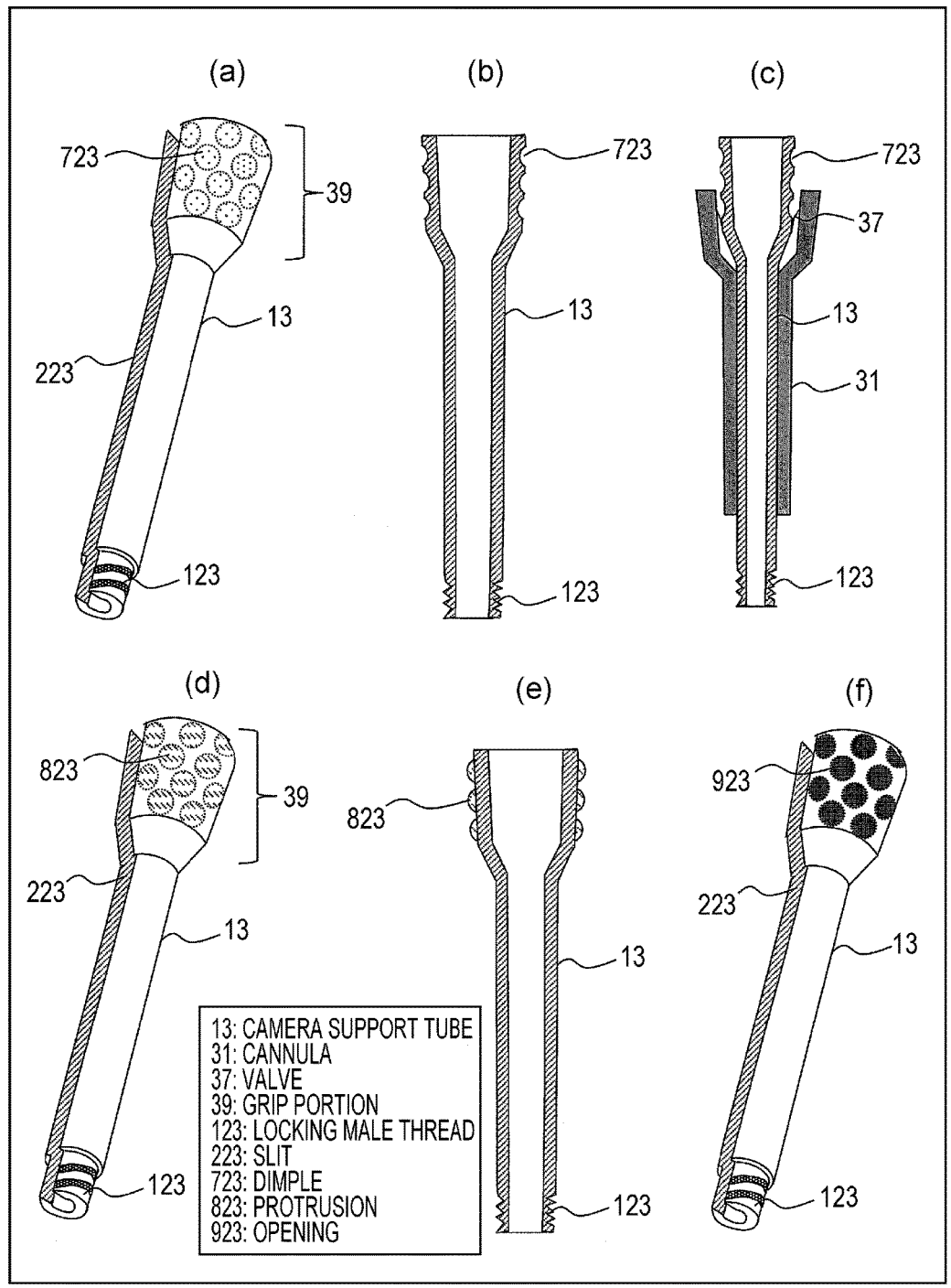
FIGS. 9(*a*), (*d*) and (*f*) are perspective views of the camera support tube of a third embodiment, and FIGS. 9(*b*), (*c*), and (*e*) are cross-sectional views thereof.
Figure 10:
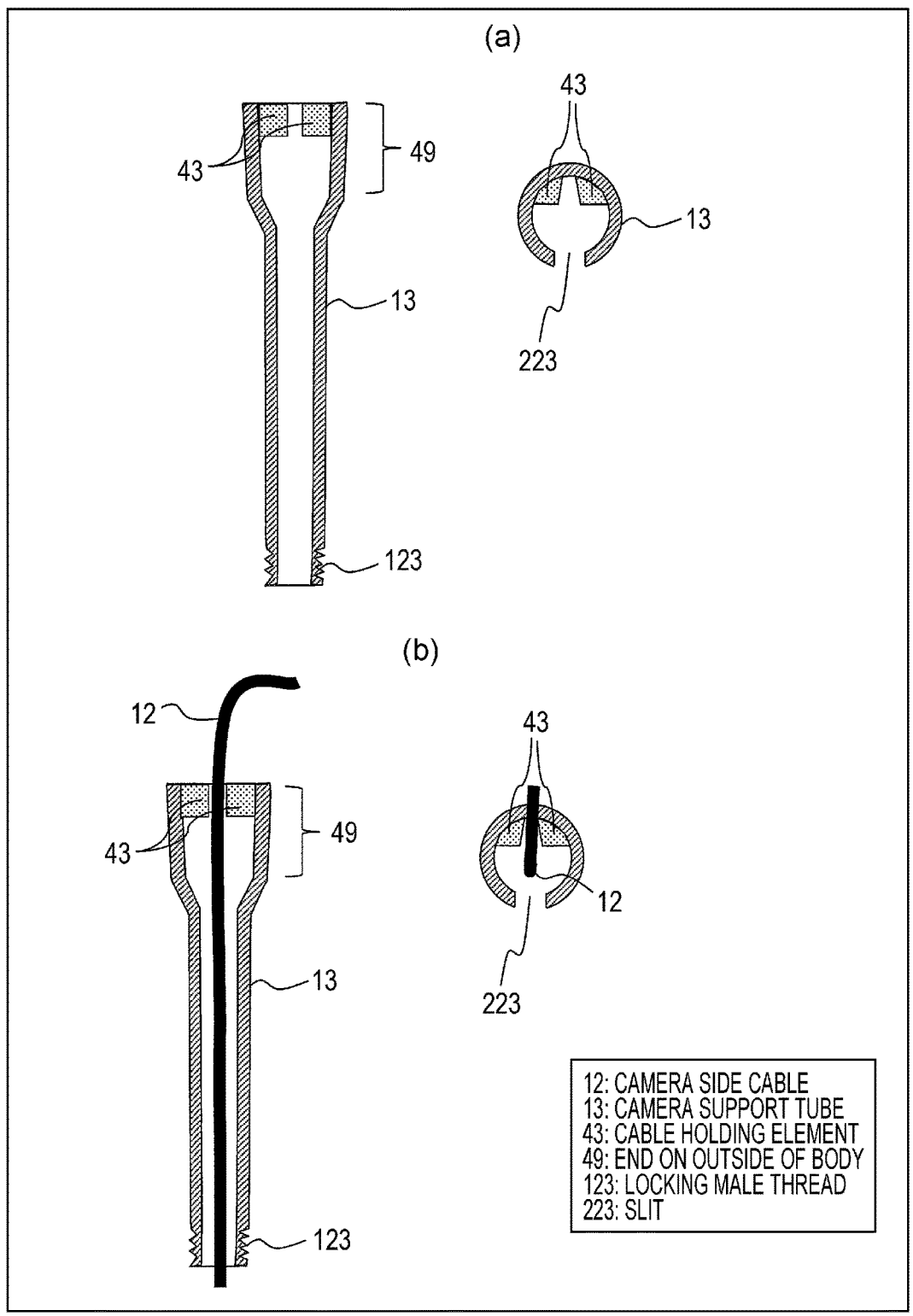
FIG. 10(*a*) is side and top cross-sectional views that illustrate a structure of the camera support tube of a fourth embodiment, and FIG. 10(*b*) is respective cross-sectional views in a state where a camera side cable is locked to the camera support tube.

After the camera unit 11 is installed in the body, as illustrated in FIG. 7, the camera side cable 12 and the apparatus side cable 16 are joined together by using the connectors 12a and 16a. Accordingly, local pictures of a treatment site are displayed on a display 18b by a camera unit control apparatus 17b, and a whole picture of an organ 42, which is photographed by the camera unit 11, is displayed on the display 18a by the camera unit control apparatus 17a.

Figure 11:
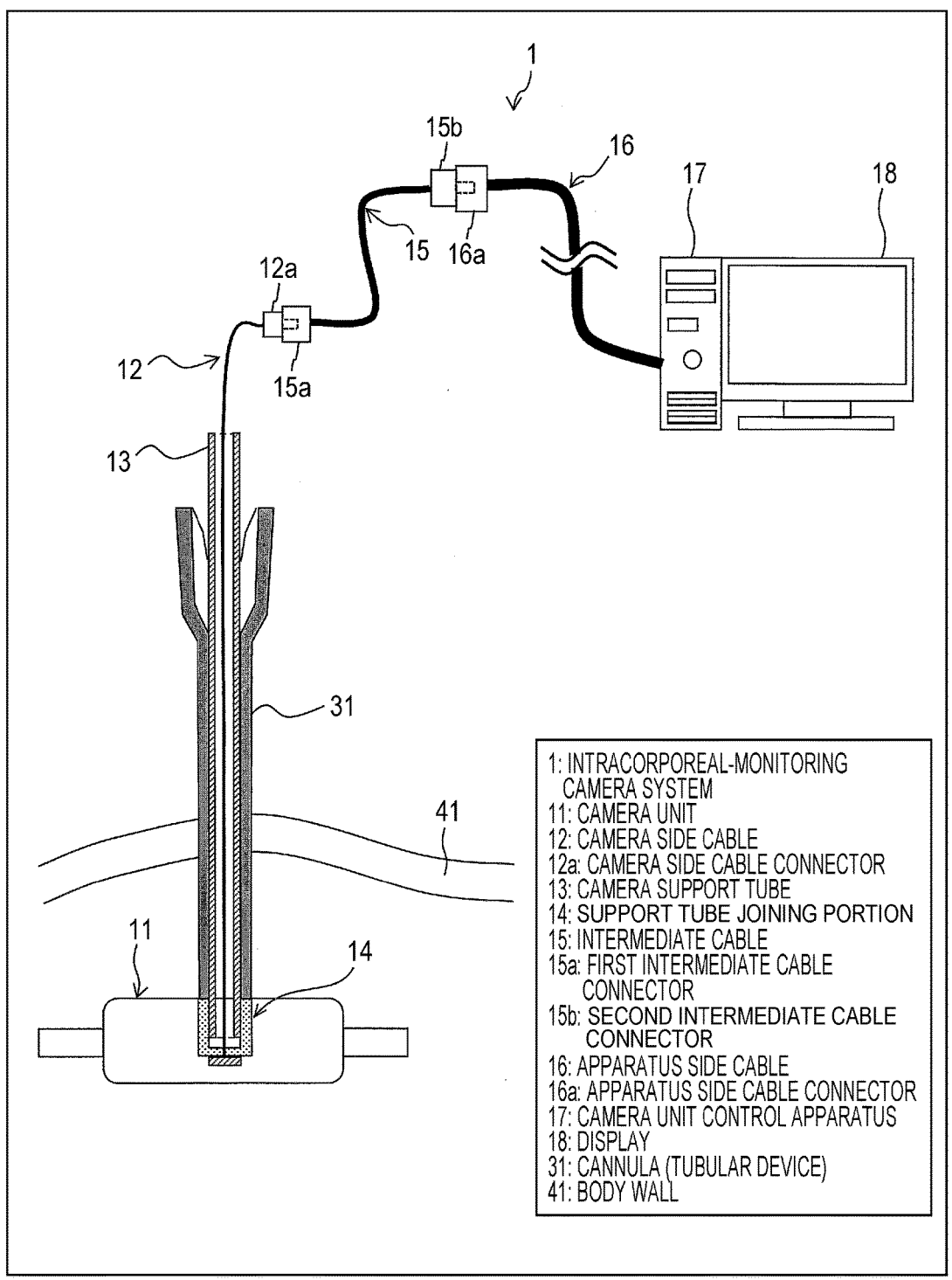
FIG. 11 is a schematic diagram that illustrates another configuration of the intracorporeal-monitoring camera system.
Figure 12:
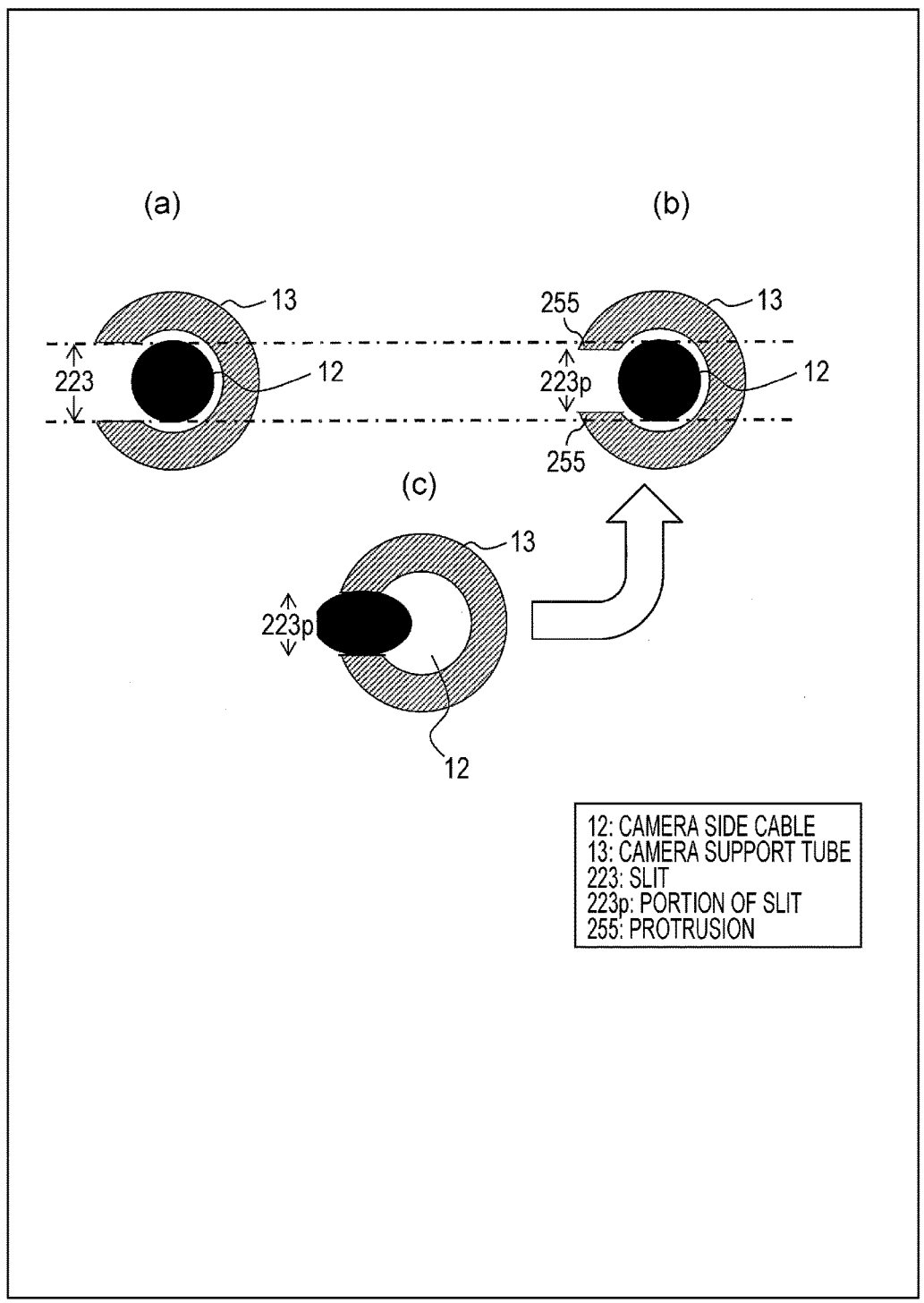
FIGS. 12(*a*) to (*c*) are cross-sectional views that illustrate a configuration example of a vicinity of a slit of the camera support tube.

As illustrated in FIG. 11, an intermediate cable 15 is preferably provided between the camera side cable 12 and the apparatus side cable 16. Accordingly, the cable diameters and the thicknesses of the cable connectors may be changed stepwise between the very thin camera side cable and the thick apparatus side cable 16, and a configuration is thereby possible which requests minimum necessary use of a small-diameter cable whose transmission rate is relatively low. Thus, the transmission rate may be increased, and high resolution images may be obtained. In this case, a camera side cable connector 12a and a first intermediate cable connector 15a of the intermediate cable 15 are fit together, and the camera side cable 12 and the intermediate cable 15 are thereby connected together. Further, the apparatus side cable connector 16a and a second intermediate cable connector 15b of the intermediate cable 15 are fit together, and the apparatus side cable 16 and the intermediate cable 15 are thereby connected together. In this example, in a case where the cable diameters and the thicknesses of the cable connectors are stepwise changed, it is preferable that the outer diameter of the camera side cable 12<the outer diameter of the intermediate cable 15<the outer diameter of the apparatus side cable 16" and "the outer diameter of the camera side cable connector 12a≤the outer diameter of the first intermediate cable connector 15a<the outer diameter of the second intermediate cable connector 15b≤the outer diameter of the apparatus side cable connector 16a" are obtained.

Further, using the intermediate cable 15 provides a significant effect of enabling a clean field and an unclean field in surgery to be effectively separated. That is, in view of the above-described transmission rate and easiness in handling in installation, the camera side cable 12 that enters the body is configured to have a minimum necessary length, and the intermediate cable 15 to which a sterilization treatment is in advance applied is used in a range from the body through the clean field to the unclean field. Accordingly, fitting between the camera side cable connector 12a of the camera side cable 12 and the first intermediate cable connector 15a may be performed in the clean field, and cleanness may be maintained. Meanwhile, the second intermediate cable connector 15b is fit in the apparatus side cable connector 16a of the apparatus side cable 16 in the unclean field, becomes unclean, and is dealt with as an unclean instrument after the fitting. Accordingly, the second intermediate cable connector 15b may completely be separated from the clean instrument side.

The sterilization treatment is performed for portions included in the "clean field" in the intracorporeal-monitoring camera system, which are maintained clean. Meanwhile, portions included in the "unclean field" are portions for which the sterilization treatment is not performed or which enter the unclean field after the sterilization treatment is performed.

The connecting strength (fitting strength) for connecting (fitting) the camera side cable 12 and the intermediate cable 15 or the apparatus side cable 16 by the connectors 12a and 15a or the connectors 12a and 16a is preferably configured lower than the bonding strength of the bonding-fixing portion that bonds and fixes the camera side cable 12 and the camera unit 11 together.

This is for enhancing safety by reducing the possibility that in a case where large force that is unexpected in usual use is applied to the cables, the bonding-fixing portion of the camera side cable 12 is broken because the connecting (fitting) portion by the connectors 12a and the 15a or the connectors 12a and 16a is first detached, or the body wall of the patient is damaged due to the camera unit 11 pulled in the direction to the outside of the body. Further, an accident may be avoided in which the operator, an assistant, or the like tumbles over the cable or the camera unit control apparatus 17 is pulled and falls from a table.

For example, specifically, the strength for connecting (fitting) the cables together by the connectors 12a and 15a or the connectors 12a and 16a is preferably equal to or smaller than 30 N (newton), which is smaller than the bonding strength of the bonding-fixing portion. In addition, an optimal range is preferably configured as a range of 4 to 10 N. In a case where the strength is configured in this range, connection may be made without applying excessively large force in connection, and excessively large force does not have to be applied in detachment.

Further, the fitting strength between the apparatus side cable connector 16a and the second intermediate cable connector 15b, which are in the unclean field, or the fitting strength between the apparatus side cable 16 and the camera unit control apparatus 17 by a cable connector (not illustrated) of the apparatus side cable 16 on the camera unit control apparatus 17 side is configured larger (for example, 50 to 100 N) than the fitting strength between the camera side cable connector 12a and the first intermediate cable connector 15a. Accordingly, in a case where unexpected force is applied to the cables, the connection between the camera side cable 12 and the intermediate cable 15 (the fitting between the camera side cable connector 12a and the first intermediate cable connector 15a) in the clean field may be configured to be necessarily released first.

Conversely, if the connection between the intermediate cable 15 and the apparatus side cable 16 (the fitting between the apparatus side cable connector 16a and the second intermediate cable connector 15b) in the unclean field is first released, for example, this leads to a risk that a portion of the intermediate cable 15 in the unclean field and the second intermediate cable connector 15b enter the clean field due to a reaction. Thus, the connection in the clean field that is first released provides a significant effect for securing safety in surgery.

In a case where the connection in the clean field is released and a portion of the intermediate cable 15 in the clean field, in other words, a portion of the intermediate cable 15 at a prescribed length from the fitting portion between the camera side cable connector 12a and the first intermediate cable connector 15a (clean portion) and the first intermediate cable connector 15a contact with the unclean field, the intermediate cable 15 may be replaced by a clean intermediate cable 15 (including a first intermediate cable connector 15a), thus maintaining safety. Further, in a case where the connector is configured with an independent and individual component and where the connector and the clean field side of the intermediate cable 15 together contact with the unclean field, the intermediate cable 15 and the connector may be replaced by clean ones.

Further, the camera side cable 12 is preferably made sufficiently short compared to the total length (approximately 1 m) of the camera side cable 12 and the above clean portion. Specifically, the camera side cable 12 is preferably equal to or shorter than half the total length of the camera side cable 12 and the above clean portion, that is, 50 cm at longest. Accordingly, entrance of the camera side cable 12 to the unclean field may be avoided. Further, the camera side cable 12 is preferably shorter than the sum of the length of the camera support tube 13 and the length of the cannula 31 (tubular device) through which the camera support tube 13 is placed.

Further, in the above-described example, a case is described where the camera side cable 12 and the apparatus side cable 16 are connected together by the intermediate cable 15. However, also in a case where the camera side cable 12 and the apparatus side cable 16 are directly connected together, the camera side cable 12 is preferably made sufficiently short compared to the total length (approximately 1 m) of the camera side cable 12 and the clean portion. In this case, the clean portion is a portion of the apparatus side cable 16 in a prescribed length from the fitting portion between the camera side cable connector 12a and the apparatus side cable connector 16a.

As described above, the operator may perform a treatment by the forceps 33a and the forceps 33c while observing the enlarged working area (local area) by the display 18b and may also perceive a state of the outside of the working area (motion of the forceps or the like on the outside of the working area, bleeding sites, residues such as gauze, and so forth) by the display 18a.

In addition, the camera unit 11 and the camera support tube 13 are joined together by high mechanical strength, and the supporting force for the camera unit 11 is larger than related art. Further, the camera side cable 12 is guided to the outside of the body through the internal portion of the camera support tube 13. Thus, after the camera unit 11 and the camera support tube 13 are joined together, a load applied to the camera side cable 12, exposure of the camera side cable 12 in the body, contact of the camera side cable 12 with the body wall 41, and so forth are avoided. This enhances the certainty of electrical connection between the camera side cable 12 and the circuit board 19 (waterproof performance and anti-fouling performance of the connecting portion). Above features enable a highly reliable intracorporeal-monitoring camera system to be realized.

Further, the operator operates the camera support tube 13 in accordance with the situation and may thereby change the direction (visual field direction) of the camera unit 11. Specifically, the operator uses elastic force of the body wall 41 to incline the camera support tube 13 and may thereby change the direction of the camera unit 11. Here, the operator takes his/her hand off the camera support tube 13, the camera support tube 13 then recovers the original direction by the elastic force, and the work efficiency of the operator may thus be improved. Further, because both of the cannula 31 and the camera support tube 13 inserted therein are cylindrical tubes, the camera support tube 13 may easily be rotated in the circumferential direction. Accordingly, the operator may change the direction of the camera unit 11 without applying a load to the body wall 41. Further, because the camera support tube 13 is retained by the cannula 31 such that the camera support tube 13 is movable in the longitudinal direction thereof (the axial direction of the tube), the operator may change an imaging zoom without applying a load to the body wall 41, by pushing the camera support tube 13 to the inside of the body or pulling the camera support tube 13 to the outside of the body. Above features enable an easy-to-use intracorporeal-monitoring camera system to be realized.

In the first embodiment, the cannula 31 and the camera support tube 13 are fixed together by the valve 37 in the cannula 31. However, in a case where a common cannula without the valve 37 is used, the cannula 31 and the camera support tube 13 may be fixed together by tape.

(Separation of Camera Unit from Camera Support Tube)

Next, a description will be made about a method of separating the camera unit 11 from the camera support tube 13. First, the operator rotates the camera support tube 13 in the opposite direction from the fitting of the threads in a state where the support portions 22 of the camera unit 11 in the body are gripped by the forceps 33a and the forceps 33c and thereby loosens the fitting between the threads. Next, the camera support tube 13 is pulled out from the support tube joining portion 14 of the camera unit 11. In addition, the operator removes the camera side cable 12 through the slit 223, separates the camera support tube 13 from the camera side cable 12 by pulling out the camera support tube 13 from the cannula 31, thereafter detaches the camera side cable connector 12a, and guides the camera unit 11 and the camera side cable 12 to the outside of the body from the trocar 32a or the trocar 32b in a state where the camera unit 11 is grasped by the forceps 33a or the forceps 33c. Alternatively, the camera unit 11 and the camera side cable 12 may be pulled out through a hole that is opened for pulling out an excised organ.

Before the camera side cable connector 12a is detached from the apparatus side cable connector 16a, work of removing the camera support tube 13 may be performed through the slit 223 in a state where the connectors 12a and 16a are connected together. Thus, a possibility that the camera side cable 12 is accidentally dropped in the body in the work and lost and has to be searched for is reduced. The work may efficiently be performed in a short time, thus providing a significant effect for an improvement in minimal invasiveness.

In a case where the camera support tube 13 is inserted and fit in the support tube joining portion 14 by using not a thread shape but a locking claw or the like, similarly in separation of the camera unit 11 from the camera support tube 13, the fitting strength between the camera support tube 13 and the support tube joining portion 14 is preferably configured lower than the bonding strength of the bonding-fixing portion that bonds and fixes the camera side cable 12 to the camera unit 11. This is because if the fitting strength between the camera support tube 13 and the support tube joining portion 14 is higher than the bonding strength of the bonding-fixing portion, large force has to be applied when the camera support tube 13 is removed from the camera unit 11, and this leads to a possibility that the bonding-fixing portion is broken or the body wall of the patient is damaged due to the camera unit 11 pulled in the direction to the outside of the body.

For example, in a case where the above fitting strength is configured in a range of 3 to 6 N, the camera support tube 13 may be removed without applying excessively large force. Further, because the hand may sense a removal action of the camera support tube 13, no excessive force is continuously applied. This provides a significant effect of safe separation.

The camera side cable connector 12a goes through the internal portion of the body in collection. However, as described above, there is not a problem because cleanness is maintained.

Second Embodiment

In the first embodiment, the slit 223 on the side surface of the camera support tube 13 is linear. However, the slit is not limited to this. FIGS. 8(a) and (b) are perspective views of the camera support tube 13 of a second embodiment. As illustrated in FIGS. 8(a) and (b), the camera support tube 13 may have a structure in which a crank type or helix type slit 223 is provided in a cylindrical tube. For example, a configuration is employed in which a lower slit 223x formed by providing a slit from one opening (on the inside of the body) of the camera support tube 13 upward in the vertical direction (the axial direction of the camera support tube 13) and an upper slit 223y formed by providing a slit from the other opening (on the outside of the body) downward in the vertical direction in a position offset from the lower slit 223x by approximately 90 degrees are coupled together by a horizontal slit 223z (crank type in FIG. 8(a)). Alternatively, a configuration is employed in which a lower slit 223x and the upper slit 223y are coupled together by a curve-shaped slit 223w (which may be an oblique slit) (helix type in FIG. 8(b)). That is, a portion of the crank type or helix type slit 223 is directed in a different direction from the axial direction (longitudinal direction) of the support tube. In FIGS. 8(a) and (b), the camera support tube 13 is rotated by approximately 90 degrees in a state where a portion of the camera side cable is placed through the lower slit 223x of the camera support tube 13, and the camera support tube 13 is inserted in the cannula such that the upper slit 223y is along the camera side cable. Accordingly, the camera side cable inserted through the slit 223 is not removed from the camera support tube 13. This further facilitates work of the operator.

In the second embodiment, the camera side cable 12 is easily inserted in the internal portion of the camera support tube 13 by the crank type or helix type slit 223 of the camera support tube 13, the work of the operator is thereby facilitated, and the work is thus performed more quickly.

Third Embodiment

The camera support tube 13 in the first and second embodiments is a cylindrical structure. However, the camera support tube is not limited to this. FIG. 9(a) is a perspective view of the camera support tube 13 of a third embodiment, and FIG. 9(b) is a cross-sectional view thereof. As illustrated in FIGS. 9(a) and (b), the camera support tube 13 may be a structure in which the end on the outside of the body, which is a grip portion 39, is thicker than the end on the inside of the body. The diameter of the grip portion 39 (thick portion) is larger than the inner diameter of the cannula 31 as illustrated in FIG. 9(c), and the camera support tube 13 may thereby be restrained from slipping down in the cannula 31. In addition, a structure is employed in which dimples 723 are provided in a periphery (surface) of the grip portion 39 (thick portion), and the camera support tube 13 is thereby made easy to hold and easy to use. The structure provided with the dimples 723 increases the surface area and contributes to diffusion of heat generated by the camera unit 11 to the outside atmosphere. Further, in order to improve work efficiency, the surface of the grip portion 39 (the end on the outside of the body as a thicker end) of the camera support tube 13 may be formed into a structure in which protrusions 823 illustrated in FIGS. 9(d) and (e) are formed. The protrusion 823 may be formed of the same material as the camera support tube 13 or other materials.

Further, mesh-shaped openings may be used instead of the dimples or the protrusions. A configuration as illustrated in FIG. 9(f) may discharge an air current generated in the above-described slit part through openings 923, and the air current may further increased. Thus, a cooling effect by the camera support tube 13 may further be enhanced. Further, weight reduction of the grip portion 39 may also be expected. This reduces difficulty in adjustment of the direction of the camera unit 11 due to a large load caused by the weight of the camera support tube 13. Further, this also reduces a change in the position that is caused by the weight after adjustment of the direction of the camera unit 11. Thus, various considerably advantageous effects such as stabilization of a camera position may be provided.

Fourth Embodiment

As illustrated in FIG. 7, the camera side cable 12 is connected with the apparatus side cable 16 via the connectors 12a and 16a. However, in order to lock the camera side cable 12 to the camera support tube 13, a cable holding element 43 (cable holder) may be formed at the end 49 on the outside of the body of the camera support tube 13 as illustrated in FIG. 10(a), which is a side view of the camera support tube. As illustrated in FIG. 10(a), which is a top view of the camera support tube, the cable holding element 43 is a structure that has a vertical groove which extends in the axial direction of the camera support tube 13 and whose width narrows from the center of the camera support tube 13 toward the outside (the direction toward the side surface) (whose cross section is an outward taper). As in FIG. 10(b), the camera side cable 12 is fixed to a bottom portion (a portion with a narrow width) of the vertical groove of the cable holding element 43 and may thereby be temporarily locked in the middle of the installation work of the camera unit 11, thereby improving work efficiency. Further, after the installation, even if the camera side cable 12 is pulled on the outside of the body, a load is not applied to the connecting portion between the camera unit 11 and the camera side cable 12, and breaking of the camera side cable 12 may thus be avoided. The cable holding element 43 may be configured with a material with elasticity.

The cable holding element 43 may be integrally formed with the camera support tube 13 or may be formed as a separate body. In a case of formation as a separate body, the camera side cable 12 is placed through the camera support tube 13, the cable holding element 43 as an individual component is thereafter inserted in the camera support tube 13, and the camera side cable 12 is held by the cable holding element 43. Accordingly, the camera side cable 12 is held by the cable holding element 43 fixed to the camera support tube 13. As a result, the camera side cable 12 is held by the camera support tube 13.

The support tube joining portion 14 may be formed into not a thread shape but a shape that is only inserted by using a locking claw or the like and may be configured to be fixed by the cable holding element 43. In this case, in order to avoid removal of the camera support tube 13 from the support tube joining portion 14 provided in the camera unit 11, the cable holding strength of the cable holding element 43 for making the camera support tube 13 hold the camera side cable 12 has to be higher than the bonding strength (fitting strength) between the camera support tube 13 and the support tube joining portion 14. Specifically, for example, in a case where the bonding strength of the inserted camera support tube 13 is set as 3 to 6 N, strength higher than this, at least 5 N or higher is necessary. Further, because the strength of the cable itself or higher is not necessary, an optimal range is preferably 5 to 50 N.

Further, the above bonding strength allows the camera support tube 13 and the support tube joining portion 14 to sufficiently contact with each other. Thus, in a case where the side surfaces of the camera support tube 13 and the support tube joining portion 14 are formed of highly heat conductive materials, heat of the camera unit 11 may efficiently be dissipated from the camera support tube 13.

CONCLUSION

An intracorporeal-monitoring camera system of a first aspect of the present invention includes: a support tube whose one end is introduced in a body; an imaging portion that is joined to the support tube in the body; a joining portion that joins the imaging portion and the support tube together; a cable that is connected with the imaging portion and drawn out to an outside of the body through the support tube; and a control system that is provided on the outside of the body, connected with the cable, and includes at least a display device, in which a slit is formed in the support tube.

A second aspect of the present invention is a configuration in the first aspect, in which a portion from which the cable is drawn out is provided in an internal portion of the joining portion, and the cable is bonded and fixed to the internal portion of the joining portion at the portion.

A third aspect of the present invention is a configuration in the first or second aspect, in which at least a portion of the slit is directed in a direction different from an axial direction of the support tube.

A fourth aspect of the present invention is a configuration in any one of the first to third aspect, in which a portion that forms a protrusion is included in an edge of the slit, a width of a portion of the slit that corresponds to the portion which forms the protrusion is smaller than a diameter of the cable.

A fifth aspect of the present invention is a configuration in the fourth aspect, in which the protrusion and another protrusion are formed as a pair on both sides of the portion of the slit.

A sixth aspect of the present invention is a configuration in any one of the first to fifth aspect, in which an external shape of a connector of the cable is larger than an inner diameter of the support tube.

A seventh aspect of the present invention is a configuration in any one of the first to sixth aspect, in which a length of the cable is smaller than a sum of a length of the support tube and a length of a tubular device through which the support tube is placed.

An eighth aspect of the present invention is a configuration in any one of the first to seventh aspect, which further includes a cable holder that holds the cable.

A ninth aspect of the present invention is a configuration in the eighth aspect, in which cable holding strength of the cable holder is higher than bonding strength between the support tube and the joining portion.

A tenth aspect of the present invention is a configuration in the ninth aspect, in which the bonding strength is in a range of 3 to 6 N.

An eleventh aspect of the present invention is a configuration in the eighth or ninth aspect, in which the cable holding strength of the cable holder is in a range of 5 to 50 N.

A twelfth aspect of the present invention is a configuration in any one of the first to eleventh aspect, in which the support tube includes a grip portion, and a surface of the grip portion has a shape with recesses and protrusions.

A thirteenth aspect of the present invention is a configuration in any one of the first to eleventh aspect, in which the support tube includes a grip portion, and plural openings are formed in a surface of the grip portion.

A fourteenth aspect of the present invention is a configuration in any one of the first to thirteenth aspect, in which a bottom portion of the joining portion in a recessed shape has a heat conductive protrusion with heat conductivity, and an inner peripheral surface of the support tube contacts with the heat conductive protrusion in a case where the imaging portion and the support tube are joined together.

A fifteenth aspect of the present invention is a configuration in the fourteenth aspect, in which the heat conductive protrusion has a shape that narrows toward an opening portion of the joining portion.

A support tube for the intracorporeal-monitoring camera system of a sixteenth aspect of the present invention is used in any one of the first to thirteenth aspects and includes a protrusion or a recess that corresponds to a shape of a protrusion or a recess which is provided in an inner wall of the joining portion.

A cable holder for the intracorporeal-monitoring camera system of a seventeenth aspect of the present invention is used in any one of the eighth to eleventh aspects, is a separate body from the support tube, and is configured to be held by the support tube.

The present invention is not limited to the above embodiments. Modes in which the above embodiments are appropriately changed based on common general technical knowledge or those obtained by combining these modes are included in embodiments of the present invention.

INDUSTRIAL APPLICABILITY

The intracorporeal-monitoring camera system is preferably used for endoscopic surgery and the like, for example.

REFERENCE SIGNS LIST

1 intracorporeal-monitoring camera system
11 camera unit (imaging portion)
12 camera side cable (cable)
12a camera side cable connector (connector)
13 camera support tube (support tube)
14 support tube joining portion
15 intermediate cable
16 apparatus side cable
16a apparatus side cable connector
17 camera unit control apparatus
18 display
19 circuit board
21 camera housing
22 support portion
23 locking female thread
25 solid-state imaging element
26 lens
27 illumination device
28 control circuit
31 cannula (tubular device)
32 trocar
33 forceps
34 endoscope
37 valve
39 grip portion
41 body wall
42 organ
43 cable holding element (cable holder)
49 end on outside of body
123 locking male thread 223 slit
323 locking hole
423, 523 locking claw
623 locking hole
723 dimple
823 protrusion
923 opening

The invention claimed is:

1. An intracorporeal-monitoring camera system comprising:
- a support tube including one end that is able to be introduced into a body;
- an imaging portion that is able to be joined to the support tube in the body;
- a joining portion that joins the imaging portion and the support tube together;
- a cable that is connected with the imaging portion and able to be drawn out to an outside of the body through the support tube; and
- a control system that is connected with the cable and includes at least a display device, wherein
- a slit is formed in the support tube so that the cable is placed in the support tube from a side of the support tube,
- the slit extends from the one end of the support tube to a second end of the support tube that is opposite to the one end, and
- a portion, from which the cable is drawn out, is provided in an internal portion of the joining portion, and the cable is bonded and fixed to the internal portion of the joining portion at the portion.

2. The intracorporeal-monitoring camera system according to claim 1, wherein a portion that forms a protrusion is included in an edge of the slit, a width of a portion of the slit that corresponds to the portion which forms the protrusion is smaller than a diameter of the cable.

3. The intracorporeal-monitoring camera system according to claim 2, wherein the protrusion and another protrusion are formed as a pair on both sides of the portion of the slit.

4. The intracorporeal-monitoring camera system according to claim 1, wherein an external shape of a connector of the cable is larger than an inner diameter of the support tube.

5. The intracorporeal-monitoring camera system according to claim 1, further comprising,
- a tubular device through which the support tube is placed, the tubular device having a length smaller than a length of the slit of the support tube, and
- a length of the cable being smaller than a sum of a length of the support tube and the length of the tubular device.

6. The intracorporeal-monitoring camera system according to claim 1, further comprising:
- a cable holder that holds the cable.

7. The intracorporeal-monitoring camera system according to claim 6, wherein cable holding strength of the cable holder is higher than bonding strength between the support tube and the joining portion.

8. The intracorporeal-monitoring camera system according to claim 7, wherein the bonding strength is in a range of 3 to 6 N.

9. The intracorporeal-monitoring camera system according to claim 6, wherein the cable holding strength of the cable holder is in a range of 5 to 50 N.

10. A cable holder that is used in the intracorporeal-monitoring camera system according to claim 6, wherein the cable holder is a separate body from the support tube and is configured to be held by the support tube.

11. The intracorporeal-monitoring camera system according to claim 1, wherein the support tube includes a grip portion, and a surface of the grip portion has a shape with recesses and protrusions.

12. The intracorporeal-monitoring camera system according to claim 1, wherein the support tube includes a grip portion, and plural openings are formed in a surface of the grip portion.

13. The intracorporeal-monitoring camera system according to claim 1, wherein a bottom portion of the joining portion in a recessed shape has a heat conductive protrusion with heat conductivity, and an inner peripheral surface of the support tube contacts with the heat conductive protrusion in a case where the imaging portion and the support tube are joined together.

14. The intracorporeal-monitoring camera system according to claim 13, wherein the heat conductive protrusion has a shape that narrows toward an opening portion of the joining portion.

15. A support tube that is used in the intracorporeal-monitoring camera system according to claim 1, the support tube comprising:
- a protrusion or a recess that corresponds to a shape of a protrusion or a recess which is provided in an inner wall of the joining portion.

16. An intracorporeal-monitoring camera system comprising:
- a support tube including one end that is able to be introduced into a body;
- an imaging portion that is able to be joined to the support tube in the body;
- a joining portion that joins the imaging portion and the support tube together;
- a cable that is connected with the imaging portion and able to be drawn out to an outside of the body through the support tube; and
- a control system that is connected with the cable and includes at least a display device, wherein
- a slit is formed in the support tube so that the cable is placed in the support tube from a side of the support tube,
- at least a portion of the slit extends in a direction different from an axial direction of the support tube, and
- a portion, from which the cable is drawn out, is provided in an internal portion of the joining portion, and the cable is bonded and fixed to the internal portion of the joining portion at the portion.

* * * * *